(12) United States Patent
Fina et al.

(10) Patent No.: US 12,049,664 B2
(45) Date of Patent: Jul. 30, 2024

(54) METHOD FOR DETECTING AND QUANTIFYING CIRCULATING DNA AND USES

(71) Applicant: CFID.Solutions, Grabels (FR)

(72) Inventors: Frédéric Fina, Greasque (FR); Philippe Pourquier, Montpellier (FR); Lise Grewis, Combaillaux (FR)

(73) Assignee: CFID.SOLUTIONS, Grabels (FR)

( * ) Notice: Subject to any disclaimer, the term of this patent is extended or adjusted under 35 U.S.C. 154(b) by 27 days.

(21) Appl. No.: 16/475,737

(22) PCT Filed: Jan. 8, 2018

(86) PCT No.: PCT/FR2018/050038
§ 371 (c)(1),
(2) Date: Jul. 3, 2019

(87) PCT Pub. No.: WO2018/127674
PCT Pub. Date: Jul. 12, 2018

(65) Prior Publication Data
US 2019/0330684 A1    Oct. 31, 2019

(30) Foreign Application Priority Data
Jan. 6, 2017 (FR) ..................... 1750146

(51) Int. Cl.
*C12Q 1/6806* (2018.01)
*C12Q 1/6886* (2018.01)

(52) U.S. Cl.
CPC ......... *C12Q 1/6806* (2013.01); *C12Q 1/6886* (2013.01); *C12Q 2600/118* (2013.01); *C12Q 2600/156* (2013.01)

(58) Field of Classification Search
CPC ............ C12Q 1/6806; C12Q 2545/113; C12Q 2521/537; C12Q 2537/165; C12Q 2561/113; C12Q 2600/118
See application file for complete search history.

(56) References Cited

U.S. PATENT DOCUMENTS

2013/0029852 A1 * 1/2013 Rava .................... C12Q 1/6809 506/2

FOREIGN PATENT DOCUMENTS

WO    WO-2014194113 A2 * 12/2014 ........... C12Q 1/6881

OTHER PUBLICATIONS

Pallisgaard et al. Clinica Chimica Acta. 2015. 446:141-146. (Year: 2015).*
Devonshire et al. Anal Bioanal Chem. 2014. 406:6499-6512. (Year: 2014).*
Risberg. "Establishment of PCR based methods for detection of ctDNA in blood". May 21, 2013. (Year: 2013).*
Benesova et al. Anal Biochem. 2013. 433:227-234. (Year: 2013).*
O'Connell et al. Laboratory Medicine. 2017. 48(4):332-338. (Year: 217).*
Aung et al., *Current status and future potential of somatic mutation testing from circulating free DNA in patients with solid tumours*, 4 Hugo J. 11-21 (2010).
Clemens et al., *A modified Phenol-chloroform extraction method for isolating circulating cell free DNA of tumor patients*, (4)1 Journal of Nucleic Acids Investigation 1-3 (2013).
Davis et al., *Detection of Circulating DNA by Counterimmunoelectrophoresis (CIE)*, 16(1) Arthritis and Rheumatism 52-58 (Jan.-Feb. 1973).
Devonshire et al., *Towards standardization of cell-free DNA measurement in plasma: controls for extraction efficiency, fragment size bias and quantification*, 406 Anal. Bioanal. Chem. 6499-6512 (2014).
Eini et al., *Chimeric External Control to Quantify Cell Free DNA in Plasma Samples by Real Time PCR*, 8(2) Avicenna Journal of Medical Biotechnology 84-90 (Apr.-Jun. 2016).
Fatouros et al., *Time of sampling is crucial for measurement of cell-free plasma DNA following acute aseptic inflammation induced by exercise*, 43 Clinical Biochemistry 1368-1370 (2010).
Galeazzi et al., *Dosage and characterization of circulating DNA: present usage and possible applications in systemic autoimmune disorders*, 2 Autoimmunity Reviews 50-55 (2003).
Giacona et al., *Cell-Free DNA in Human Blood Plasma: Length Measurements in Patients with Pancreatic Cancer and Healthy Controls*, 17(1) Pancreas 89-97 (1998).
Gormally et al., *Circulating free DNA in plasma or serum as biomarker of carcinogenesis: Practical aspects and biological significance*, 635 Mutation Research 105-117 (2007).
Jin et al., *Overview of Cell Death Signaling Pathways*, 4(2) Cancer Biology & Therapy 139-163 (Feb. 2005).

(Continued)

Primary Examiner — Joseph G. Dauner
(74) Attorney, Agent, or Firm — Panitch Schwarze Belisario & Nadel LLP; Erin M. Dunston

(57) ABSTRACT

The invention relates in particular to a method for detecting and/or quantifying cell-free DNA from a sample of biological fluid of a patient of interest, comprising at least: (i) a step of extracting cell-free DNA from a sample of biological fluid to which at least one effective quantity of a first exogenous DNA fragment having 50-2000 base pairs, preferably 50-200 base pairs, preferably 60-160 base pairs, even more preferably 70-150 base pairs and better still 80-140 base pairs (ICE), is added; (ii) a step of amplifying and quantifying the cell-free DNA extracted in step (i) and the exogenous DNA fragment ICE; and (iii) a step of standardising the amount of cell-free DNA extracted, comprising the calculation of a first ratio (Grewis) of the number of copies of cell-free DNA to the number of copies of the first fragment of exogenous DNA (ICE), and the uses thereof for the purpose of diagnosis, prognosis or theragnosis, or for monitoring the progress of a specific physiological state of a patient of interest likely to release circulating DNA.

13 Claims, 5 Drawing Sheets

Specification includes a Sequence Listing.

(56) References Cited

OTHER PUBLICATIONS

Laktionov et al., *Extracellular Circulating Nucleic Acids in Human Plasma in Health and Disease*, 23(6&7) Nucleosides, Nucleotides & Nucleic Acids 879-883 (2004).

Lipson et al., *Circulating tumor DNA analysis as a real-time method for monitoring tumor burden in melanoma patients undergoing treatment with immune checkpoint blockade*, 2(42) Journal for Immunotherapy of Cancer 1-7 (2014).

Lo et al., *Presence of fetal DNA in maternal plasma and serum*, 350 Lancet 485-487 (Aug. 16, 1997).

Luke et al., *Realizing the Potential of Plasma Genotyping in an Age of Genotype-Directed Therapies*, 106(8) JNCI 1-5 (Aug. 8, 2014).

Oxnard et al., *Noninvasive detection of response and resistance in EGFR-mutant lung cancer using quantitative next-generation genotyping of cell-free plasma DNA*, 20(6) Clin. Cancer Res. 1698-1705 (Mar. 15, 2014).

Rapisuwon et al., *Circulating biomarkers to monitor cancer progression and treatment*, 14 Computational and Structural Biotechnology Journal 211-222 (2016).

Reinert et al., *Analysis of circulating tumour DNA to monitor disease burden following colorectal cancer surgery*, 65 BMJ 625-634 (2016).

Sanmamed et al., *Quantitative Cell-Free Circulating $BRAF^{V600E}$ Mutation Analysis by Use of Droplet Digital PCR in the Follow-up of Patients with Melanoma Being Treated with BRAF Inhibitors*, 61(1) Clinical Chemistry 297-304 (2015).

Steinman, *Circulating DNA in Systemic Lupus Erythematosus Isolation and Characterization*, 73 J. Clin. Invest. 832-841 (Mar. 1984).

Velders et al., *Exercise is a potent stimulus for enhancing circulating DNase activity*, 47 Clinical Biochemistry 471-474 (2014).

Wyllie et al., *Cell Death: The Significance of Apoptosis*, 68 International Review of Cytology 251-306 (1980).

Wyllie, *Glucocorticoid-induced thymocyte apoptosis is associated with endogenous endonuclease activation*, 284 Nature 555-556 (Apr. 10, 1980).

\* cited by examiner

SEQUENCE LISTING

```
<160> NUMBER OF SEQ ID NOS: 11

<210> SEQ ID NO 1
<211> LENGTH: 300
<212> TYPE: DNA
<213> ORGANISM: artificial
<220> FEATURE:
<223> OTHER INFORMATION: 1st exogenous DNA fragment 300bp coding for the
      precursor of a Pro-aggregating serine protease from Cerastes
      cerastes

<400> SEQUENCE: 1
cctaatgaca cttatcccaa agtccctcat tgtgctaaca ttaacatact tgagcattcg        60
ctgtgtgaaa gagcttacaa tgatctttcg gcgagtagca gaacattgtg tgcaggtatc      120
gaaaaaggag gcatagatac atgtaagggt gactctgggg gacccctcat ctgtaatgga      180
caaatccagg gcattgtatc ttggggagat gaagtttgtg gtaaacctaa taagcctggc      240
gtctatacca aggtctttga ttatactgac tggatccgga acattattgc aggaaataca      300

<210> SEQ ID NO 2
<211> LENGTH: 110
<212> TYPE: DNA
<213> ORGANISM: artificial
<220> FEATURE:
<223> OTHER INFORMATION: 2nd exogenous DNA fragment 110bp coding for the
      precursor of a Pro-aggregating serine protease from Cerastes
      cerastes

<400> SEQUENCE: 2
gctgaacaaa ccagttaaca acagtacaca catcgcgcct ctcagcttgc cttccagtcc       60
tcccagtgtg ggctcagatt gccgtattat gggatggggc acaatcacat                 110

<210> SEQ ID NO 3
<211> LENGTH: 22
<212> TYPE: DNA
<213> ORGANISM: artificial
<220> FEATURE:
<223> OTHER INFORMATION: sense primer for the 1st fragment

<400> SEQUENCE: 3
tggacaagga catcatgctg at                                                22

<210> SEQ ID NO 4
<211> LENGTH: 20
<212> TYPE: DNA
```

```
<213> ORGANISM: artificial
<220> FEATURE:
<223> OTHER INFORMATION: antisense primer for the 1st fragment

<400> SEQUENCE: 4
gactggaagg caagctgaga                                              20

<210> SEQ ID NO 5
<211> LENGTH: 30
<212> TYPE: DNA
<213> ORGANISM: artificial
<220> FEATURE:
<223> OTHER INFORMATION: labeled probe for the 1st fragment

<400> SEQUENCE: 5
aaccagttaa caacagtaca cacatcgcgc                                   30

<210> SEQ ID NO 6
<211> LENGTH: 18
<212> TYPE: DNA
<213> ORGANISM: artificial
<220> FEATURE:
<223> OTHER INFORMATION: sense primer for the human RPP-30 gene

<400> SEQUENCE: 6
gatttggacc tgcgagcg                                                18

<210> SEQ ID NO 7
<211> LENGTH: 20
<212> TYPE: DNA
<213> ORGANISM: artificial
<220> FEATURE:
<223> OTHER INFORMATION: antisense primer for the human RPP-30 gene

<400> SEQUENCE: 7
gagcggctgt ctccacaagt                                              20

<210> SEQ ID NO 8
<211> LENGTH: 16
<212> TYPE: DNA
<213> ORGANISM: artificial
<220> FEATURE:
<223> OTHER INFORMATION: labeled probe for the human RPP-30 gene

<400> SEQUENCE: 8
ctgacctgaa ggctct                                                  16

<210> SEQ ID NO 9
<211> LENGTH: 24
<212> TYPE: DNA
<213> ORGANISM: artificial
<220> FEATURE:
<223> OTHER INFORMATION: sense primer for the 2nd fragment

<400> SEQUENCE: 9
atgacactta tcccaaagtc cctc                                         24

<210> SEQ ID NO 10
<211> LENGTH: 21
<212> TYPE: DNA
<213> ORGANISM: artificial
<220> FEATURE:
<223> OTHER INFORMATION: antisense primer for the 2nd fragment

<400> SEQUENCE: 10
caatgttctg ctactcgccg a                                            21
```

```
<210> SEQ ID NO 11
<211> LENGTH: 20
<212> TYPE: DNA
<213> ORGANISM: artificial
<220> FEATURE:
<223> OTHER INFORMATION: labeled probe for the 2nd fragment

<400> SEQUENCE: 11
catacttgag cattcgctgt                                          20
```

METHOD FOR DETECTING AND QUANTIFYING CIRCULATING DNA AND USES

REFERENCE TO SEQUENCE LISTING SUBMITTED ELECTRONICALLY

This application contains a sequence listing, which is submitted electronically via EFS-Web as an ASCII formatted sequence listing with a file name "Sequencelisting", creation date of Apr. 25, 2020, and having a size of about 3 KB. The sequence listing submitted via EFS-Web is part of the specification and is herein incorporated by reference in its entirety.

CROSS-REFERENCE TO RELATED APPLICATIONS

This application is a U.S. National Stage Application pursuant to 35 U.S.C. § 371 of International Patent Application PCT/FR2018/050038, filed on Jan. 8, 2018, and published as WO 2018/127674 on Jul. 12, 2018, which claims priority to French Patent Application 1750146, filed on Jan. 6, 2017, all of which are incorporated herein by reference in their entireties for all purposes.

FIELD OF THE INVENTION

The field of the invention relates to a process for detecting and quantifying cell-free DNA (also generally called 'circulating DNA or 'circulating free DNA, cfDNA') and use thereof in particular for the diagnosis, prognosis or monitoring of the physiological state of a given subject of interest.

STATE OF THE ART

It has been known for many years that blood plasma contains small amounts of circulating free DNA, about 10 nanograms per milliliter, a concentration that can rise significantly, up to 0.5 micrograms per milliliter, in cancer patients. Several studies have shown that it is possible to use this circulating DNA to detect genetic modifications specific to cancer processes such as microsatellite mutations and alterations (lung, colorectal, head and neck cancers). However, the prevalence of these genetic alterations in circulating DNA varies according to the diseases and genes studied (Pierre Hainaut, m/s no. 3, vol. 16, March 2000).

If circulating DNA concentrations are at present not or little used as a diagnostic or prognostic tool, it is because of the lack of standardization of extraction and assay methods that would make it possible to establish these standardized thresholds. Pre-analytical "good practices" specific to circulating DNA have been published. In particular, they recommend working with plasma collected in tubes (EDTA, Streck, Roche), centrifuging the blood tube no later than 6 hours after collection (up to 24 hours depending on the testing centers), storing the plasma between −20° C. (storage<1 month) and −80° C. (storage>1 month), storing the extracted circulating DNA at −20° C. (in a screw-cap tube) and avoiding repeated freeze-thaw cycles.

However, pre-analytical considerations that influence the analytical result must include other factors such as the volume of plasma to be extracted, directly correlated to the amount of DNA extracted, the efficiency of the extraction technique for a given volume of liquid, the reproducibility of the extraction, the final concentration of the DNA and the inter-test standardization of the efficiency/concentration of the eluate obtained.

Due to the relative ease of access and the nature of the sample, the use of cell-free DNA (also called circulating DNA) has been predicted for some years now for monitoring the progression or response of patients to cancer treatments (Aung K L et al., Hugo J 2010) or others. The term "liquid biopsy" has emerged to describe the monitoring of the genetic evolution of the tumor from blood (Fatouros I G et al., ClinBiochem 2010).

Concentrations of circulating DNA indeed reflect both pathological and physiological processes (Fatouros I G, et al. ClinBiochem 2010). Circulating extracellular DNA can be detected in healthy controls (Fatouros I G, et al. ClinBiochem 2010) and malignant controls (Oxnard G R et al., Clin Cancer Res 2014; Lipson E J et al., J Immunother Cancer 2014; Reinert T et al., Gut 2016) or non-malignant (Steinman C R. J Clin Invest 1984; Galeazzi M, et al. AutoimmunRev 2003). In addition, trauma (Laktionov P P, et al., Nucleosides Nucleotides NucleicAcids 2004), therapeutic procedures (Davis G L, Jr., Davis J S., Arthritis-Rheum 1973) and pregnancy (Lo Y M et al., 1997) may also result in the release of free DNA into the circulation. Many factors can therefore influence the level of circulating DNA in the plasma. Monitoring the response to treatments by regular blood tests has real advantages.

Thus, if the amount of circulating DNA per ml of liquid can be considered as a biomarker of a clinical response, standardization of the amount of circulating DNA extracted from one extraction to another is essential.

In addition to standardizing the amount of DNA extracted, maintaining the size profile of circulating DNA samples is important and can be crucial for the biological validation of results. Indeed, the size of circulating DNA fragments in healthy controls comes essentially from apoptotic cells. The lengths of circulating DNA fragments are generally 185 to 200 bp (Giacona M B et al., Pancreas 1998). This uniformly truncated circulating DNA is produced by enzymatic cleavage during apoptosis (Wyllie A H, Nature 1980). The size of circulating DNA from malignant cells varies greatly, because in addition to apoptosis, necrosis and autophagy are responsible for the death of cancer cells (Jin Z and EI-Deiry W S, Cancer BiolTher 2005). The size of the circulating DNA fragments is therefore different between healthy and pathological individuals.

It is important that circulating DNA extraction techniques maintain the size profile of circulating DNA, particularly small fragments that can be removed if the proportion of the mixture of chemical components in the binding step on the silica column varies. The composition of the liquid can also change this proportion. It is therefore essential to be able to verify and normalize the extraction efficiency of small fragments, especially around 100 base pairs.

Other parameters are also to be considered, particularly DNA extraction efficiency (total quantity), elution volume and concentration of these circulating DNA.

Indeed, the amount of circulating DNA is directly proportional to the amount of plasma extracted. It is therefore important to extract as much plasma as possible. The total volume to be extracted, including plasma, proteases and binding solutions, exceeds on average 10 ml (per 4 ml of plasma) and must be eluted on silica columns not exceeding 1 to 2 cm in height and 1 cm in diameter. It should be noted that the smaller the diameter of the column, the smaller the elution volume, and thus the more concentrated the circulating DNA extract.

Furthermore, the number of analyses to be performed on this type of sample can be very large; it is therefore essential to obtain elution volumes that will allow numerous analyses to be performed with sufficient concentrations of circulating DNA. The two are contradictory.

Finally, obtaining a concentrated solution is essential because the analytical sensitivity is directly dependent on the quantity of circulating DNA analyzed.

The volume of liquid to be extracted, the concentration and the elution volume are interdependent.

To the Applicant's knowledge, there are currently no kits and devices for extracting, amplifying and quantifying DNA, in particular cell-free DNA, which address these various issues.

Moreover, since the work of P. Mandel and P. Métais in 1948, it has been clearly established that blood carries a small amount of circulating free DNA from the release of genetic material from tissues. This circulating free DNA (cfDNA) is in the form of double-stranded DNA with an average size of 150-180 bp corresponding to the wrapping of the DNA around the nucleosome, the larger sizes correspond to multiples of 150-180 bp. Its lifespan is less than two hours, before it is filtered and removed from the bloodstream by the spleen, liver and kidneys. All studies agree that cfDNA is detected in smaller quantities in healthy individuals and that its increase is related to different clinical situations such as stroke, myocardial infarction, intensive muscle exercise, acute renal failure, liver cytolysis, trauma, surgery, graft rejection and cancer.

The origin of cfDNA is not yet fully elucidated but is thought to be linked to three phenomena: apoptosis, necrosis and, to a lesser extent, active secretion. In healthy individuals, circulating DNA comes mainly from apoptotic cells (Giacona, M. B. et al., Pancreas, 1998). The DNA fragment lengths in this case are generally 185 to 200 bp (Wyllie, A. H. et al., Int Rev Cytol, 1980). In contrast, in cancer tissues, the size of circulating DNA varies greatly, because in addition to apoptosis, necrosis and autophagy are responsible for cancer cell death (Jin, Z. et al., Cancer Biol Ther, 2005). Fragments can reach 450-500 bp corresponding to the wrapping of DNA around three nucleosomes. Beyond these sizes, even larger fragments, which are most often considered to result from contamination by leukocyte DNA, may also be present. However, the origin of these high-weight fragments is not clearly elucidated. It is possible to distinguish circulating DNA populations by measuring the size of long and short fragments. These are next-generation sequencing (NGS) approaches using specific bioinformatics processes to measure cfDNA size. Jiang P and Lo Y M find opportunities in many applications, particularly in the field of cancer research and transplantation (Trends Genet. 2016). Nevertheless, it is currently impossible, in clinical routine, to ascertain the somatic origin (tumor, transplant, etc.) and the release process of circulating DNA (apoptosis, necrosis, etc.).

One of the major pitfalls of cfDNA analysis relates to pre-analytical processes (processing of blood tubes and DNA extraction). Variations in cfDNA concentrations can be artefactually produced by the release of leukocyte DNA before the first centrifugation of the tubes, or in the absence of a second centrifugation at 4000 g or higher. In addition, in order to use cfDNA concentrations expressed as ml/plasma to monitor a response to treatments, it is important to ensure the robustness of the extraction technique, but above all to propose a method to normalize extractions between one another and over time.

The inventors have precisely developed a process for detecting and quantifying DNA whether cell-free or not, in particular cell-free DNA (circulating DNA), including an extraction step in which calibrants, also known as standards (exogenous DNA fragments), are added to standardize variations in circulating DNA in patients, and optionally to verify the reproducibility of extraction of small circulating DNA.

According to the invention, 'calibrants' or 'standards' means internal controls of the process for detecting and quantifying extracted circulating DNA, said calibrants or standards consisting of the exogenous DNA fragments defined below. The terms calibrated ICE fragment and ICE fragment will also be used hereinbelow.

'Calibrated ICE fragment' means, according to the invention, an exogenous DNA fragment whose concentration is calibrated by ddPCR; this calibrated ICE fragment can be used to normalize the concentration of free genomic DNA (cfDNA) by calculating the cfDNA/ICE ratio (Grewis) in order to ensure that only physiological and/or pathological fluctuations in this circulating DNA in a subject of interest are measured by comparing other analytical points over time or in comparison with a control (healthy subject).

'Exogenous DNA fragment' means a DNA fragment of a different species than the circulating DNA of interest; preferentially, a non-human exogenous DNA fragment will be selected for the extraction of circulating human genomic DNA.

'Circulating DNA' refers to cell-free DNA. In the rest of the description, the terms cell-free DNA and circulating DNA (cfDNA) will be used interchangeably. According to a particular embodiment, it will be human circulating DNA, in particular circulating DNA from a subject of interest.

According to the invention, 'subject of interest' means a subject distinct from a normal or healthy subject. In particular, the subject of interest is a subject likely to release cell-free DNA, in particular related to apoptosis, necrosis and/or to a lesser extent active secretion. Such a subject of interest may in particular be a subject with or at risk of developing a cancer or a clinical condition selected notably from stroke or myocardial infarction, acute renal failure, hepatic cytolysis, trauma, surgery, graft rejection, or a subject undergoing intensive muscle exercise, or a subject undergoing medical treatment such as biopsy, surgery, radiotherapy, chemotherapy, immunotherapy, or active principle (chemical or biological).

The process for detecting and quantifying circulating DNA using an extraction step in which calibrants or standards are added according to the invention, has the following advantages according to the embodiments described below:

Superior coverage of fragmented DNAs for sensitive applications;

Control of extraction efficiency by standardization (exogenous internal control ICE thanks to the first exogenous DNA fragment of 50-2000 base pairs);

Optionally control of extraction efficiency for sizes close to 100 base pairs (LED thanks to the second optional exogenous DNA fragment of 50-150 base pairs);

Optimization of elution efficiency of circulating DNA (in the presence of albumin or gelatin); and/or Concentration of the elution of circulating DNA (ultrafiltration), Co-amplification of the exogenous internal control and a genomic DNA sequence (e.g., mutated DNA in oncology or 'donor' DNA in the case of transplantation).

It is also advantageous, in particular for the preferred embodiments of the invention, because of its practicality and time saving thanks to the accessories above the extraction columns (allowing the entire sample/solution mixture to be loaded at once, thus limiting cross-contamination), its internal quality control (lyophilized culture medium as control sample), its reproducibility (albumin, gelatin or substitutes in the elution step), and the concentration of circulating DNA (ultrafiltration).

SUMMARY OF THE INVENTION

A first object of the invention is a process for detecting and/or quantifying cell-free DNA from a biological fluid sample from a subject of interest, comprising at least:
(i) a step of extracting cell-free DNA from a biological fluid sample in which has been added at least
  a) an effective amount of a first exogenous DNA fragment of 50-2000 base pairs, preferably 50-200 base pairs, preferably 60-160 base pairs, more preferably 70-150 base pairs and better 80-140 base pairs (ICE), and
  b) optionally an effective amount of a second exogenous DNA fragment of 50-150 base pairs (LED) of distinct sequence from the first exogenous DNA fragment;
(ii) a step of amplifying and quantifying the cell-free DNA and the exogenous ICE and/or LED DNA fragments extracted in step (i), and
(iii) a step of standardizing the amount of extracted cell-free DNA and optionally its size profile including:
  calculating a first ratio of the copy number of cell-free DNA to the copy number of exogenous DNA fragment of 50-2000 base pairs, preferably 50-200 base pairs, preferably 60-160 base pairs, more preferably 70-150 base pairs and better 80-140 base pairs (ICE), and
  optionally calculating a second ratio of the copy number of the first exogenous DNA fragment of 50-2000 base pairs (ICE) to the copy number of the second exogenous DNA fragment of 50-150 base pairs (LED).

"Effective amount' of exogenous DNA fragment means an amount (or a copy number for a given size of the fragment) of exogenous DNA per ml of biological fluid sample allowing the implementation of the step of standardizing the amount of extracted circulating DNA and optionally its size profile. According to a particular embodiment, the amount of exogenous DNA per ml of biological fluid sample is at least 1 fg or even 2 fg per ml of sample (or 10,000 to 20,000 copies per ml of plasma sample for a 110 base pair fragment), in particular ranging from 1 fg or 2 fg to 2 ng per ml of sample.

These concentrations of calibrants, near or below the concentrations of copies of genes of cell-free DNA from a normal subject (e.g., less than 8 ng/ml), make it possible to work with the physiological values of a healthy subject in order to accurately measure fluctuations.

Step (i) of extracting cell-free DNA from a biological fluid sample will generally comprise in succession a step of proteolysis of said biological sample, a step of isolating circulating free DNA, and an elution step, optionally precipitation and optionally concentration of circulating free DNA.

Step (ii) of amplifying and quantifying the cell-free DNA extracted in the previous step will preferably be performed by a digital PCR, qPCR and/or NGS method.

According to a particular embodiment of the invention, it is possible to co-amplify in the same well the exogenous DNA fragment and a human sequence detected by ddPCR or TaqMan qPCR or NGS. This is referred to as 'co-amplification' or co-detection.

The process according to the invention also makes it possible to perform multiplex dPCR or NGS with this calibrant (ICE) and gene abnormalities (mutations, amplifications, etc.) in order to monitor changes in the concentration of abnormalities over time or compared to a reference subject (healthy subject, control).

'Reference subject (control, healthy subject)' means a 'normal' subject, distinct from the subject of interest, meaning not likely to be affected or to develop a clinical indication as described for the subject of interest.

Step (iii) of standardization, characteristic of the detection and quantification process of the invention, is used to measure in a simple and reliable way the amount of circulating free DNA extracted and its variations over time (new extractions and quantifications from a biological fluid sample from the same subject at defined times t0, t1, t2, etc.) or compared to a reference subject (control, healthy subject), and optionally its size profile to verify the reproducibility of the extraction of circulating DNA in the specific size range, in particular circulating DNA of around 100 base pairs in size.

Another object of the invention relates to the use of the process for detecting and/or quantifying cell-free DNA from a biological fluid sample from a subject of interest according to the invention, in a method for analyzing a biological sample from a subject of interest likely to release cell-free DNA, in particular a subject of interest affected by or likely to develop a cancer or a clinical condition selected in particular from stroke or myocardial infarction, acute renal failure, hepatic cytolysis, trauma, surgery, graft rejection, or a subject undergoing intensive muscular exercise, or a subject undergoing medical treatment such as biopsy, surgery, radiotherapy, chemotherapy, immunotherapy, or active principle.

The invention also relates to an in vitro process for the analysis, in particular the diagnosis, prognosis, theranosis, or the monitoring of changes in a specific physiological state of a subject of interest likely to release circulating DNA, in particular a subject of interest affected or likely to develop a cancer or a clinical condition selected in particular from stroke or myocardial infarction, acute renal failure, hepatic cytolysis, trauma, surgery, graft rejection, or a subject undergoing intensive muscle exercise, or a subject undergoing medical treatment such as biopsy, surgery, radiotherapy, chemotherapy, immunotherapy, or active principle, comprising the following steps:
(i) at a time t0, detecting and/or quantifying cell-free DNA from a biological fluid sample from a subject of interest according to the process of the invention as described above;
(ii) at a time t1, repeating step (i), and
  a. comparing the ratio (Grewis) of the copy number of circulating DNA to the copy number of exogenous DNA fragment of 50-2000 base pairs, preferably 50-200 base pairs, preferably 60-160 base pairs, more preferably 70-150 base pairs and better 80-140 base pairs (ICE), obtained at time t1, with the same ratio obtained at time t0.

Steps (ii) and (iii) can be repeated as many times as necessary (for example at t2, t3, t4, etc.) to monitor changes in a specific physiological state of a subject of interest, and consequently the effect of medical treatment (surgery, drugs, radiotherapy, etc.) on said subject.

These measurements can easily be made from a blood sample collected from the subject (blood draw).

The time elapsed between two measurement times (t0 and t1, t1 and t2, etc.) may generally represent one or a few hours, days, weeks, months or years, depending on the physiological state of the subject of interest and the objective sought by quantifying circulating DNA from a biological fluid sample from said subject.

The skilled person will thus be able to adapt this time elapsed between two measurement times according to the physiological state of the subject of interest and any medical treatments followed in order to define t1, t2 and following times in relation to a given t0.

The in vitro analysis process according to the invention is intended in particular to:
- analyze fluctuations in cell-free DNA to monitor response and/or resistance to medical treatment such as biopsy, surgery, radiotherapy, chemotherapy, immunotherapy, or active principle, or
- analyze fluctuations in cell-free DNA to monitor the occurrence of graft rejection, or
- analyze fluctuations in cell-free DNA to decide whether to conduct a subsequent analysis of genomic abnormalities, or
- monitor changes in the concentration of mutated DNA, or monitor changes in the concentration of 'donor' DNA.

Alternatively, the invention relates to an in vitro process for the diagnosis, prognosis, theranosis of a subject of interest likely to release circulating DNA, in particular a subject of interest affected or likely to develop a cancer or a clinical condition selected in particular from stroke or myocardial infarction, acute renal failure, hepatic cytolysis, trauma, surgery, graft rejection, or a subject undergoing intensive muscle exercise, or a subject undergoing medical treatment such as biopsy, surgery, radiotherapy, chemotherapy, immunotherapy, or active principle, comprising the following steps:
- (i) at a time t, detecting and/or quantifying cell-free DNA from a biological fluid sample from a subject of interest according to the invention;
- (ii) comparing the ratio (Grewis) of the copy number of circulating DNA to the copy number of exogenous DNA fragment of 50-2000 base pairs, preferably 50-200 base pairs, preferably 60-160 base pairs, more preferably 70-150 base pairs and better 80-140 base pairs (ICE), obtained at time t, with the same ratio obtained in a reference subject (healthy subject, control).

Another object of the invention is a kit or set for extracting cell-free DNA from a biological fluid sample from a subject of interest, comprising:
- (i) At least a first exogenous DNA fragment of 50-2000 base pairs, preferably 50-200 base pairs, preferably 60-160 base pairs, more preferably 70-150 base pairs and better 80-140 base pairs (ICE);
- (ii) Buffers and enzymes, in particular a cell-free DNA proteolysis buffer, proteolysis enzyme, binding buffer, wash buffer, and elution buffer,
- (iii) Devices for isolating cell-free DNA, in particular silica membrane extraction columns and advantageously extraction columns surmounted by loading accessories, preferably funnels,
- (iv) Multi-well plates, in particular 24-well DeepWell 25 ml plates
- (v) Screw-cap tubes, preferably 1.5 ml, and
- (vi) A user manual,
said exogenous ICE DNA fragment being provided in said kit or provided separately to said kit, forming an extraction set.

According to a particular embodiment, the loading accessories used in step (iii) are accessories that surmount the extraction columns and have at least one diameter greater than the diameter of said column, making it possible to load the entire sample/extraction solution mixture at once. In particular, such accessories allow volumes ranging from 0.5 to 100 ml to be loaded into the column, in particular from 1 ml to 36 ml, preferentially from 1 ml to 14 ml. According to a particular embodiment, the volume will be from 0.5 to 8 ml, notably from 0.5 to 4 ml.

These accessories can have different shapes. According to a particular and preferred embodiment, funnels will be used as accessories to load the entire sample/extraction solution mixture.

'Extraction solution' means the solution containing the buffers and enzymes necessary for the circulating DNA extraction step.

According to a particular embodiment, the cell-free DNA extraction kit according to the invention is used in combination with a cell-free DNA amplification and quantification kit, supplied together or separately. The cell-free DNA amplification and quantification kit will generally comprise at least:
- (i) specific sense and antisense primers for the cell-free DNA of the subject of interest and for the exogenous DNA fragment as defined in the invention, for the amplification step,
- (ii) labeled probes for the cell-free DNA of the subject of interest and for the exogenous DNA fragment as defined in the invention, for the detection and quantification step,
- (iii) reaction buffers,
- (iv) multi-well plates and
- (v) a user manual.

The invention further relates to the use of at least a first exogenous DNA fragment of 50-2000 base pairs, preferably 50-200 base pairs, preferably 60-160 base pairs, more preferably 70-150 base pairs and better 80-140 base pairs (ICE), for use in standardizing a method for extracting and quantifying cell-free DNA and/or in a method for analyzing fluctuations in cell-free DNA in a subject of interest over time by measuring the ratio (Grewis) of the copy number of cell-free DNA to the copy number of the first exogenous DNA fragment of 50-2000 base pairs, preferably 50-200 base pairs, preferably 60-160 base pairs, more preferably 70-150 base pairs and better 80-140 base pairs (ICE).

Said exogenous DNA fragment can advantageously be used with any kit for extracting and/or quantifying DNA whether cell-free or not, preferably cell-free DNA.

DETAILED DESCRIPTION OF THE INVENTION

Process for Detecting and/or Quantifying Circulating DNA

The invention therefore relates to a process for detecting and/or quantifying cell-free DNA from a biological fluid sample from a subject of interest, comprising at least:
- (i) a step of extracting cell-free DNA from a biological fluid sample in which has been added at least an effective amount of a first exogenous DNA fragment of 50-2000 base pairs, preferably 50-200 base pairs, preferably 60-160 base pairs, more preferably 70-150 base pairs and better 80-140 base pairs (ICE);

(ii) a step of amplifying and quantifying the cell-free DNA and the exogenous ICE DNA fragment extracted in step (i), and (iii) a step of standardizing the amount of extracted cell-free DNA comprising calculating a first ratio (Grewis) of the copy number of cell-free DNA to the copy number of the first exogenous DNA fragment of 50-2000 base pairs, preferably 50-200 base pairs, preferably 60-160 base pairs, more preferably 70-150 base pairs and better 80-140 base pairs (ICE).

In particular, the subject of interest is a subject affected by or likely to develop a cancer or a clinical condition selected among stroke or myocardial infarction, acute renal failure, hepatic cytolysis, trauma, surgery, graft rejection, or a subject undergoing intensive muscular exercise, or a subject undergoing medical treatment such as biopsy, surgery, radiotherapy, chemotherapy, immunotherapy, or active principle (chemical or biological).

According to a particular embodiment, the subject of interest is likely to have cancer.

According to another particular embodiment, the subject of interest is likely to have a graft rejection.

According to another particular embodiment, the subject of interest is subjected to medical treatment selected from biopsy, surgery, radiotherapy, chemotherapy, immunotherapy, or an active principle (chemical or biological).

According to a particular embodiment, the biological fluid is selected from the group consisting of whole blood, serum, plasma, urine, saliva, bone marrow effluent, lymph, cerebrospinal fluid, tear fluid, sweat, milk, aqueous humor, synovial fluid, pleural fluid, peritoneal fluid, amniotic fluid, bile, seminal fluid, expectorations.

Preferably, the biological fluid is plasma.

Plasma samples are generally prepared from whole blood.

In order to limit the release of cellular DNA (circulating cells) causing the dilution of cell-free DNA, protocols including two centrifugations should preferably be used.

According to a preferred embodiment, whole blood is collected, for example on Cell-Free DNA BCT® (Streck), Roche (Ariosa) and EDTA K3 tubes, according to the suppliers' recommendations.

Advantageously, the following will be performed:
a $1^{st}$ centrifugation (1200-1600 g) at room temperature (20° C.±5° C.) performed within a maximum period of 6 hours after collection; the plasma (supernatant) is recovered without taking the layer of cells separated between the plasma and the red blood cells;
a $2^{nd}$ centrifugation (3000-16000 g) at room temperature (20° C.±5° C.); the plasma is aspirated without taking the formed pellet.

Regardless of the tubes mentioned above, the plasma can be stored at −20° C. for up to 1 month or at −80° C. for periods longer than 1 month.

The main steps of the process according to the invention are detailed below.

Extraction of Circulating DNA

In particular, the extraction step (i) will comprise the following steps:

(i1) Proteolysis of said biological fluid sample from a subject of interest after adding to said sample at least an effective amount of a first exogenous DNA fragment of 50-2000 base pairs, preferably 50-200 base pairs, preferably 60-160 base pairs, more preferably 70-150 base pairs and better 80-140 base pairs (ICE) and optionally an effective amount of a second exogenous DNA fragment of 50-150 base pairs (LED), (i2) Isolation of cell-free DNA, in particular by affinity on a membrane support, preferably a silica membrane support in an extraction column, (i3) Elution of the cell-free DNA isolated in step (i2) in an aqueous phase, (i4) Optionally precipitation of the cell-free DNA, (i5) Advantageously concentration of the cell-free DNA, (i6) Optionally preservation and/or storage of said cell-free DNA.

According to a particular embodiment, the extraction step (i) does not include a precipitation step (i4).

According to a particular embodiment of the invention, the process of the invention comprises co-amplification of a cell-free DNA, an exogenous ICE fragment and a genomic DNA sequence selected from a mutated DNA sequence or a 'donor' DNA sequence.

According to the invention, 'mutated DNA sequence' means a sequence with a mutation. In the case of cancer, for example, the aim will be to detect/quantify activating mutations or mutations for resistance to a targeted therapy. In the case of prostate cancer, the aim will be to detect/quantify mutations in the gene encoding the androgen receptor for resistance to abiraterone treatment or other targeted therapies. In the case of non-small cell lung cancer (NSCLC), the aim will be to detect/quantify activating mutations in the gene encoding EGFR or mutations for resistance to osimertinib or other targeted therapy.

According to the invention, "donor" DNA sequence means a DNA sequence from the donor (case of transplant) as opposed to the recipient's DNA, by targeting SNP or other HLA sequences.

Each step of the extraction method is specified in the following description.

(i1) Proteolysis of Said Biological Sample

The standard(s) (exogenous DNA fragments mentioned above), characterizing the process for extracting, amplifying and quantifying circulating DNA of the invention, are added to the biological fluid sample from a subject of interest before the proteolysis step.

At least the first exogenous DNA fragment of 50-2000 base pairs, preferably 50-200 base pairs, preferably 60-160 base pairs, more preferably 70-150 base pairs, preferably 70-150 base pairs and better 80-140 base pairs (ICE) and optionally the second exogenous DNA fragment of 50-150 base pairs (LED), as defined according to the invention, are added. According to a particular embodiment, their mixture will be used. According to another particular and preferred embodiment, only the first ICE fragment will be used provided it is small in size, i.e. 50 to 200 base pairs, preferably 60 to 160 base pairs, preferably 70 to 150 base pairs, and better 80 to 140 base pairs. At these small sizes, the ICE fragment therefore advantageously also plays the role of the LED fragment.

The first exogenous DNA fragment of 50-2000 base pairs, preferably 50-200 base pairs, preferably 60-160 base pairs, more preferably 70-150 base pairs and better 80-140 base pairs is used as the exogenous internal control (ICE).

The skilled person will define the size of the first exogenous DNA fragment to be used according to the subject of interest whose circulating DNA is to be quantified and according to the analytical technique (quantification) available.

According to a particular and preferred embodiment, this first exogenous DNA fragment may have a size ranging from 50 to 200 base pairs, preferably 60 to 160 base pairs, preferably 70 to 150 base pairs, and better from 80 to 140 base pairs.

According to another particular embodiment, the first exogenous DNA fragment (ICE) is a fragment of preferably 200 to 1000 base pairs, more preferably 250 to 350 base pairs.

According to a particular embodiment of the invention, the first exogenous DNA fragment is a non-human DNA fragment of 300 base pairs.

According to a particular and preferred embodiment of the invention, the first exogenous DNA fragment is a non-human DNA fragment of 110 base pairs.

This inter-test standard (ICE) makes it possible to standardize the amount of extracted circulating DNA and its inter-test variations (and in particular over time for the same subject of interest) or compared to the amount of extracted circulating DNA in a reference subject (healthy subject, control) by calculating the ratio (Grewis) of the copy number of circulating DNA to the copy number of a first exogenous DNA fragment of 50-2000 base pairs, preferably 50-200 base pairs, preferably 60-160 base pairs, more preferably 70-150 base pairs and better 80-140 base pairs (ICE). These values are obtained after extraction, amplification and quantification of said exogenous DNA fragments, in parallel with the amplification and quantification of the circulating DNA, as described below in the description.

The value of the ratio is expressed in arbitrary units (Grewis). This approach thus avoids having to adjust calculations for eluate volumes.

This first exogenous DNA fragment of 50-2000 base pairs can be used alone or in combination with the second exogenous DNA fragment of 50-150 base pairs, distinct from the first fragment.

The second exogenous DNA fragment of 50-150 base pairs, distinct from the first fragment, is used to control small fragments (LED).

According to a particular embodiment, the second exogenous DNA fragment is an exogenous DNA fragment of 80-120 base pairs.

According to a particular embodiment of the invention, the second exogenous DNA fragment is a non-human DNA fragment of 110 base pairs.

This second exogenous DNA fragment (LED) makes it possible to verify the reproducibility of extraction of circulating DNA in the specific size range, i.e. to standardize the size profile of the extracted circulating DNA, and to avoid the influence of the chemical/biological composition of the plasma on the extraction efficiency of small size fragments. The ratio of the copy number of the first exogenous DNA fragment of 50-2000 base pairs (ICE) to the copy number of the second exogenous DNA fragment of 50-150 base pairs (LED) is calculated.

According to a particular and preferred embodiment, only a first ICE fragment of 50 to 200 base pairs, preferably 60 to 160 base pairs, preferably 70 to 150 base pairs, and better 80 to 140 base pairs, will be used, which will also play the role of the LED fragment.

The step of proteolysis or hydrolysis of proteins under the action of enzymes is generally performed in the presence of a buffer and enzymes.

According to a particular embodiment, an enzyme (proteinase K) and a lysis buffer (LYS) will be used. The skilled person will determine the amounts of enzyme and lysis buffer to be used based on the volume of sample to be processed. According to a particular embodiment, the mixture, once vortexed, is incubated at an enzyme activation temperature, in particular a temperature of 56° C.±5° C. for 30 minutes to 1 hour with shaking.

According to a particular embodiment, the lysis buffer contains chaotropic salts (guanidinium hydrochloride); these salts disrupt the macromolecules and allow water molecules to be separated from the silica and DNA once the molecules are charged. It can create a bridge favorable for the binding of DNAs and standards on the silica.

According to a preferred embodiment, the process for detecting and/or quantifying cell-free DNA according to the invention further implements in the extraction step (i) at least one control sample preferably consisting of a lyophilisate of culture medium of a mutated or non-mutated cell line, to be rehydrated to mimic the biological fluid sample.

In particular, a mutated cell line is defined as a cell line whose genome has modifications such as single-nucleotide variants (SNVs), deletions, insertions, copy-number variations (CNVs), etc.

This quality control of the extraction efficiency makes it possible to verify the inter-test reproducibility of the extraction by calculating the same two ratios on this control sample, respectively the ratio of the copy number of circulating DNA to the copy number of the first exogenous DNA fragment of 50-2000 base pairs and the ratio of the copy number of the first exogenous DNA fragment of 50-2000 base pairs (ICE) to the copy number of the second exogenous DNA fragment of 50-150 base pairs (LED), which must not vary from one extraction series to another.

The control sample according to the invention undergoes the same reactions as the biological fluid sample from the subject of interest from which circulating DNA is to be extracted, in particular the addition of standards (exogenous ICE and LED DNA fragments, extraction, amplification, quantification and control).

(i2) Isolation of Circulating DNA The isolation of circulating DNA can be performed using one of the following methods:
  a. By affinity of circulating DNA for a support (silica membrane, magnetic beads, etc.), preferably a silica membrane support, or
  b. By extraction method between two immiscible liquid phases (phenol/chloroforms, TRIzol, Piotr Chomczynski and Nicoletta Sacchi methods)
  c. By density gradient (for example cesium chloride, etc.).

According to a particular embodiment, the affinity method will be used on a membrane support, preferably a silica membrane support in an extraction column.

MIDI columns are preferably used according to the supplier's recommendations, in the presence of activation and binding buffers.

According to a particular embodiment, the step of isolating and binding circulating DNA on the silica membrane support consists in:
  applying the silica membrane activation buffer in each MIDI column, incubating and then applying vacuum (−0.4 bar);
  adding a binding buffer per ml of plasma to each lysed sample;
  mixing the contents of the tube by drawing/expelling at least 5 times;
  placing the funnels on each column;
  applying the lysed sample mixture to the MIDI columns;
  applying vacuum at −0.4 bar for 5 minutes, making sure that all the lysate has passed through the column.

The activation and binding buffers are the buffers used in standard extraction protocols.

According to a particular embodiment, a guanidinium hydrochloride-ethanol binding buffer will be used.

According to a preferred embodiment of the process for detecting and/or quantifying cell-free DNA according to the invention, the extraction column in the cell-free DNA isolation step (i2) is surmounted by a loading accessory, preferably a funnel, allowing the entire sample/extraction solution mixture, i.e. a volume ranging from preferably 1 ml to 14 ml, to be loaded.

This configuration allows all (manual) or half (automated) of the plasma-proteolysis buffer-binding solution mixture to be handled in a single pipetting operation.

The step of isolating and binding circulating DNA is followed by a membrane washing step according to the supplier's standard recommendations (several washing cycles, application of vacuum at −0.4 bar for 5 minutes).

(i3) Elution of Circulating DNA

According to a particular embodiment, before eluting the circulating DNA, the vacuum, for example at least −0.6 bar for 10 minutes, is applied to completely dry the membrane of any trace of ethanol.

An elution buffer is then added according to the supplier's recommendations.

According to a preferred embodiment of the process for detecting and/or quantifying cell-free DNA according to the invention, the step (i3) of eluting the cell-free DNA isolated in step (i2) is performed in the presence of an elution buffer supplemented with albumin, gelatin, or substitutes.

This advantageously increases the extraction efficiency and stabilizes the reproducibility of the eluted volume.

According to a first embodiment, the elution step is performed in the presence of an elution buffer supplemented with albumin, such as bovine serum albumin (BSA), preferably at 0.5 mg/ml eluate.

According to another preferred embodiment, the elution step is performed in the presence of an elution buffer supplemented with gelatin, such as that marketed by SIGMA under the trade name Prionex®, preferably used at 1%.

(i4) Optionally Precipitation and (i5) Concentration of Circulating DNA

According to a particular embodiment, the extraction process does not comprise a precipitation step (i4). According to a preferred embodiment of the process for detecting and/or quantifying cell-free DNA according to the invention, the step (i5) of concentrating the pure cell-free DNA is performed on a concentration plate by ultrafiltration.

This concentration step can be performed by excluding the aqueous phase, and advantageously without adding chaotropic salts for the binding and alcohol washing of the circulating DNA.

The volume to be concentrated can range from 20-300 µl, the volume to be recovered can range from 25-300 µl.

(i6) Preservation and/or Storage of Circulating DNA

The circulating DNA obtained must be stored at 5° C.±3° C. if the digital PCR (dPCR) or droplet digital PCR (ddPCR) or quantitative PCR (qPCR) is performed following, otherwise the circulating DNA must be stored at −80° C. for longer storage.

According to a particular preferred embodiment of the invention, the cell-free DNA extraction step is performed according to the following steps:

(i1) proteolysis of the plasma, and in parallel of the control sample (CQI), in which the standard(s) (exogenous ICE and LED DNA fragments), with proteinase K and lysis buffers containing guanidinium hydrochloride chaotropic salts, have been added;

(i2) isolation of cell-free DNA on a silica membrane, in the presence of a guanidinium hydrochloride-ethanol binding buffer, added in large volume to fix the DNA to the silica, the % ethanol affecting the size of the fragments retained. The volume is added to the silica column equipped with a removable funnel in one step in manual mode and in two steps in automatic mode. Three washing steps are necessary to remove inhibitors and salts. Then drying for 10 minutes removes the ethanol present on the silica membrane;

(i3) elution of the free DNA by a first step in which the free DNA is desorbed by an EDTA-free buffer weakly buffered at pH 8.5. Advantageously, the extraction step according to the invention does not provide for the addition of entraining RNA that could interfere with certain subsequent applications such as amplification with the NGS method. Elution is preferably performed in buffer supplemented with albumin or gelatin, which optimizes the volume and yield of the extracted DNA.

(i4) and (i5) the eluate can be concentrated by ultrafiltration if necessary, for downstream applications.

Processes with the extraction step for Streck Cell-free DNA BCT® blood collection tubes have also been developed. The stabilizing reagents in BCT® tubes require prolonged proteolysis to effectively isolate circulating DNA.

Amplification and Quantification of Circulating DNA

This step of amplification and quantification of the cell-free DNA and the exogenous DNA fragment(s) (ICE and optionally LED standards) extracted in the previous step, can be performed by methods well known to the skilled person.

According to a particular embodiment, the process of the invention allows co-amplification, in particular in the same well, of an exogenous ICE fragment and a genomic sequence having a mutation or a DNA sequence from the donor (transplantation), allowing changes in the concentration of mutated DNA or 'donor' DNA to be monitored between two extractions over time.

According to preferred embodiments, it can be performed by a digital PCR, qPCR (real-time quantitative PCR) and/or next-generation sequencing (NGS) method, according to the suppliers' recommendations.

Preferentially, digital PCR (dPCR) will be used for its ability to multiplex amplifications, its sensitivity, its absolute quantification, its high resolution for variations in amount obtained according to the Poisson law.

qPCR will be used as a substitute when dPCR is not available.

Finally, NGS, with its reading depth capability, will be used instead to quantify exogenous DNA (ICE and LED) and genomic DNA.

According to a particular embodiment, DNA will be absolutely quantified using a PCR system comprising:

A system for amplifying extracted circulating DNA comprising sense and antisense primers to amplify a region of the human genome and specific probes, advantageously labeled with fluorophores, for detecting amplified circulating DNA;

A system for amplifying the extracted first exogenous DNA fragment (ICE) comprising sense and antisense primers to amplify said first fragment and specific probes, advantageously labeled with fluorophores, for detecting said first amplified exogenous DNA fragment (ICE);

Optionally a system for amplifying the extracted second exogenous DNA fragment (LED) comprising sense and antisense primers to amplify said second fragment and specific probes, advantageously labeled with fluorophores, for detecting said second amplified exogenous DNA fragment (LED).

The absolute quantified values for each DNA (circulating DNA, exogenous ICE and optionally LED DNA fragments), extracted from a biological fluid sample from a subject of interest, a reference subject (healthy subject, control) or a control sample, respectively, will make it possible to calculate the ratios according to the step of standardizing the amount of extracted cell-free DNA and optionally its size profile described below.

Standardization of the Amount of Extracted Cell-Free DNA

The step of standardizing the amount of extracted cell-free DNA and optionally its size profile, characteristic of the process for detecting and quantifying circulating DNA according to the invention, comprises, for DNA extracted from the biological fluid sample and, advantageously in parallel, for DNA extracted from the control sample:
- calculating a first ratio (Grewis) of the copy number of cell-free DNA to the copy number of the first exogenous DNA fragment of 50-2000 base pairs, preferably 50-200 base pairs, preferably 60-160 base pairs, more preferably 70-150 base pairs and better 80-140 base pairs (ICE), and
- optionally calculating a second ratio of the copy number of the first exogenous DNA fragment of 50-2000 base pairs (ICE) to the copy number of the second exogenous DNA fragment of 50-150 base pairs (LED), After each DNA extraction, amplification and quantification, the Grewis (first ratio) is calculated for the biological fluid sample (e.g., plasma) and for the control sample and, optionally, the extraction efficiency of small fragments around 80-120 bases (second ratio) is verified.

The value of the first ratio (Grewis) serves as a reference that can be compared between each extraction and thus defines the variations in the amount of circulating DNA in a given subject over time or in a subject of interest compared to a reference (healthy subject, control).

If the value of the first ratio (Grewis) increases between two extractions, it means that the amount of circulating DNA in the subject increased between the first and second extraction.

If the value of the first ratio (Grewis) decreases between two extractions, it means that the amount of circulating DNA in the subject decreased between the first and second extraction.

If the value of the first ratio (Grewis) for a subject of interest is higher than the same ratio for a reference (healthy subject, control), this means that the amount of circulating DNA in the subject of interest is higher, indicating active apoptosis, necrosis and/or secretion.

The value of the second ratio, in contrast, must not vary from one extraction to another.

The numerical values are not important; for example, a value of the second ratio equal to 1 should be selected, i.e. identical proportions of the first exogenous DNA fragment (ICE) and the second exogenous DNA fragment (LED).

If the second ratio increases, this means that the DNA of small size has not been extracted correctly, and that the results obtained on the quantification of circulating DNA are biased.

Uses

Another object of the invention relates to the use of a process for detecting and/or quantifying cell-free DNA from a biological fluid sample from a subject of interest according to the invention, in a method for analyzing a biological sample from a subject of interest likely to release cell-free DNA, in particular a subject suffering from or likely to develop a cancer or a clinical condition selected in particular from stroke or myocardial infarction, acute renal failure, hepatic cytolysis, trauma, surgery, graft rejection, or a subject undergoing intensive muscular exercise, or a subject undergoing medical treatment such as biopsy, surgery, radiotherapy, chemotherapy, immunotherapy, or active principle (chemical or biological).

This process for detecting and/or quantifying cell-free DNA according to the invention may be used in particular in methods of in vitro analysis of biological fluid samples (e.g., blood plasma) from the subject of interest for diagnostic, prognostic, theranostic, or monitoring changes in a specific physiological state of an individual.

According to a preferred particular embodiment, this process for detecting and/or quantifying cell-free DNA according to the invention will be used to monitor changes in a specific physiological state of an individual under treatment, for example surgical treatment, or medicinal treatment (e.g., drugs), or radiotherapy treatment or any other method causing cell death inducing variation in the amount of cell-free DNA.

By way of example, it is possible to measure, for a subject of interest likely to release circulating DNA, for example a subject suffering from or likely to develop cancer, and from a biological fluid sample (plasma), at a time t0 of its life, the value of the first ratio (Grewis).

This value at t0 can have a biological value for the diagnosis of a pathology, prognosis of a medical event (metastasis, recurrence of the disease, death, etc.), in particular compared to a reference subject (control, healthy subject) and/or response to medical treatment (surgery, drugs, radiotherapies, etc.).

Thus, by measuring this ratio (Grewis) at different times t1, t2, t3, etc. during the life of said subject of interest, the variations of this ratio can be monitored, indicating an increase or decrease in the amount of circulating DNA in said subject. These are longitudinal variations (over time) in the amount of circulating DNA in said subject of interest.

The invention therefore also relates to an in vitro process for the diagnosis, prognosis, theranosis, or the monitoring of changes in a specific physiological state of a subject of interest likely to release circulating DNA, in particular a subject suffering from or likely to develop a cancer or a clinical condition selected in particular from stroke or myocardial infarction, acute renal failure, hepatic cytolysis, trauma, surgery, graft rejection, or a subject undergoing intensive muscle exercise, or a subject undergoing medical treatment such as biopsy, surgery, radiotherapy, chemotherapy, immunotherapy, or active principle (chemical or biological) comprising the following steps:
(i) at a time t0, detecting and/or quantifying cell-free DNA from a biological fluid sample from a subject of interest according to the process of the invention as described above;
(ii) at a time t1, repeating step (i), and
(iii) comparing the ratio (Grewis) of the copy number of circulating DNA to the copy number of exogenous DNA fragment of 50-2000 base pairs, preferably 50-200 base pairs, preferably 60-160 base pairs, more preferably 70-150 base pairs and better 80-140 base pairs (ICE), obtained at time t1, with the same ratio obtained at time t0.

Steps (ii) and (iii) can be repeated as many times as necessary (for example at t2, t3, t4, etc.) to monitor changes in a specific physiological state of a subject of interest, and consequently the effect of medical treatment (surgery, drugs, radiotherapy, etc.) on said subject.

Alternatively, the invention relates to an in vitro process for the diagnosis, prognosis, theranosis of a subject of interest likely to release circulating DNA, in particular a subject suffering from or likely to develop a cancer or a clinical condition selected in particular from stroke or myocardial infarction, acute renal failure, hepatic cytolysis, trauma, surgery, graft rejection, or subject to intensive muscle exercise, or subject to medical treatment such as biopsy, surgery, radiotherapy, chemotherapy, immunotherapy, or active principle (chemical or biological) including at least the following steps:

(i) at a time t, detecting and/or quantifying cell-free DNA from a biological fluid sample from a subject of interest according to the process for detecting and/or quantifying cfDNA according to the invention; and (ii) comparing the ratio (Grewis) of the copy number of circulating DNA to the copy number of exogenous DNA fragment of 50-2000 base pairs, preferably 50-200 base pairs, preferably 60-160 base pairs, more preferably 70-150 base pairs and better 80-140 base pairs (ICE), obtained at time t, with the same ratio obtained in a reference subject (healthy subject, control).

The description will now illustrate a few applications of the process according to the invention.

Applications in the Field of Oncology

Major therapeutic advances have been made in recent years with the development of MAP-kinase inhibitors (tyrosine kinase inhibitors: TKIs) and immune checkpoint inhibitors (anti-CTLA4 and anti-PD1; immunotherapies). Given the cost and toxicity of these molecules, and the increasing complexity of treatment regimens, it is increasingly essential to be able to benefit from biomarkers to guide therapeutic choices in order to optimize management and limit toxicities. Less than a decade ago, several teams demonstrated high levels of circulating DNA in patients with gastric, ovarian or prostate cancer. Due to the relative ease of access and nature of the sample, the use of cfDNA has in recent years been anticipated to become a tool to assist in monitoring patients' progress or response to cancer treatments (Aung, K. L et al., Hugo J; 2010).

To date, cfDNA can thus be used in clinical research to analyze somatic mutations of genes of therapeutic interest in certain diseases such as non-small cell lung cancers, colon cancers, thyroid cancers, and melanomas. But as of today, only osimertinib (Astra Zeneca) is authorized for the treatment of adult patients with locally advanced or metastatic non-small cell lung cancer (NSCLC) with the EGFR T790M mutation. The MA specifies that the EGFR T790M mutation status is determined by a validated analytical method using circulating tumor DNA (ctDNA) obtained from a plasma sample. Many analytical methods (targeted or non-targeted) can be used to search for gene abnormalities from cfDNA. It is thus possible to detect copy-number abnormalities (CNA), point mutations, insertions, deletions, insertions/deletions, genome methylations by targeted methods: qPCR, pyrosequencing, high-resolution melting (HRM) curve, MassARRAY, SnapShot, dPCR, etc. or non-targeted techniques: CGH-array, SNP-array, Sanger sequencing, NGS, etc. These analyses can be used to provide a prognosis, a diagnosis or even to predict the response to curative treatment. Apart from the sensitivity problems that are not only inherent in analytical performance but also in cfDNA concentration and mutation, it is not possible to date to make a typical analytical result "normal" because there is no routine clinical method to ensure the presence of tumor DNA. In this case the result is made "non-contributory" and a new solid or liquid biopsy is required. cfDNA can be detected in healthy controls and subjects with non-malignant conditions, trauma (Laktionov, P. P. et al., 2004), therapeutic procedures (Davis, G. L. et al., Arthritis Rheum, 1973) and sports practice (Velders M. et al., Clinical Biochemistry, 2014) can also result in the release of DNA into the bloodstream. As a result, the identification of cancer-specific genetic markers is a guarantee to only monitor tumor DNA (Luke, J. J. et al., J Natl Cancer Inst, 2014). The approach used by some laboratories for the analysis of tumor cfDNA is to look for individual somatic genomic abnormalities as markers of tumor pathology. Taking the example of melanoma, the BRAF V600E variant can thus allow the monitoring of treatments with BRAF-specific inhibitors (Sanmamed, M. F. et al., Clin Chem, 2015). In this case, the choice of target is obvious, but does not allow a global approach to the pathology since only about 50% of patients have the V600 mutation and the variant monitored is the target of the treatment and therefore subject to drug pressure. Other, rarer mutations can also be analyzed. This approach, however, is complex, costly and difficult to perform in routine diagnosis because it must be adapted to the molecular profile of each patient, which means performing exome NSG analyses. Thus, no pre- or post-analytical technique can ensure the presence of contributing material, and therefore, for each new liquid biopsy an analysis is performed without any selective criteria.

The process of the invention thus has three applications in the field of oncology:

1—Monitoring Response to Treatment by Measuring the Fluctuation in Total cfDNA Over Time:

Analysis of cfDNA fluctuations to monitor the response to treatment (surgery, radiotherapy, chemotherapy and other active principles including targeted therapies such as immunotherapies) by quantifying circulating DNA released by the cell death/lysis of the tumor, its metastases or their periphery. The extraction technique according to the invention, IDXtract (ID-Solutions, France), makes it possible to be free from the constraints previously stated, thanks to the addition in the plasma to be extracted of calibrated exogenous DNA: ICE (non-human sequence). The ICE fragment undergoes the extraction steps and ensures the efficiency of the extraction. The qPCR/dPCR kit according to the invention, IDQuant (ID-Solutions, France), makes it possible to co-amplify exogenous ICE DNA with one or more human genome sequences. It is possible to determine the amount of cfDNA and ICE for the same test sample and to calculate the value of the cfDNA/ICE ratio and express it per ml of plasma (cfDNA/ICE/ml plasma=Grewis). The variation in Grewis over time for the same subject of interest ensures that fluctuations in cfDNA of physiological/pathological origin can be monitored longitudinally without artefacts.

2—Monitoring a Mutation:

The detection/quantification of genomic abnormalities concomitant with the measurement of Grewis and/or the exogenous ICE sequence alone makes it possible to monitor changes in the concentration of mutated DNA between the different liquid biopsies performed longitudinally. The results are normalized to the ICE fragment (added to the plasma before cfDNA extraction) calibrated by dPCR, expressed per ml of plasma and/or Grewis. Mutant variations make it possible, for example, to track the increase over time in the mutated cfDNA sequence linked directly or indirectly to the emergence of tumor cell clones resistant to targeted or non-targeted treatment, in progress. For example, it is possible to define a decision threshold value for changing the therapeutic line.

3—the Role of Analytical 'Hub' Before Genomic Analysis:

The analysis of somatic genomic abnormalities from tissues is performed only after ensuring that tumor cells are present in the sample. As previously explained, in the case of liquid biopsies and particularly plasma, there is no method to ensure the presence of circulating tumor DNA in the total free DNA (cfDNA) sample. There is no method to ensure that the results will be contributory before genomic analysis is performed. The use of Grewis variations according to the invention makes it possible to play the role of analytical "hub":

Decrease or no variation in Grewis: no genomic analysis required;

Increase in Grewis: genomic analysis recommended.

Applications in the Field of Transplantation

Although short-term successes after solid organ transplantation are convincing, the incidence of acute rejection varies between types of transplants. Acute discharges are observed for intestinal, cardiac, and pulmonary transplants (approximately 55%, 30-45% and 35-40%, respectively). For liver, simultaneous kidney-pancreas, and acute renal transplantation, rejection is less frequent with incidences, 2 years after transplantation, of 4-6%, 13-30%, 20%, and 12-14%, respectively.

Thus, even for long-term transplantation, the survival of the recipient remains unsatisfactory. Despite the prescription of immunosuppressive drugs (ISDs), excessive or insufficient immunosuppression may occur. In the case of pancreatic, kidney and liver transplants, the measurement of blood markers such as lipase/amylase, serum creatinine and liver enzymes, respectively, is recommended for routine post-transplant monitoring. However, in the field of kidney transplantation, deterioration of graft function cannot be detected until significant damage occurs. After heart transplantation, monitoring of cardiac enzymes is not recommended due to the low sensitivity of these markers in the diagnosis of acute rejection.

Non-invasive detection of rejects appears of even greater interest in the case of infra-clinical rejections, which are currently only detectable from biopsies. Currently, AlloMap® is the only commercially available non-invasive organ transplant monitoring test. This is an RT-qPCR test of the expression profile of 11 genes, based on peripheral blood mononuclear cells (PBMCs), validated in heart transplant recipients. It is used in heart transplant follow-up to detect acute rejection in patients between 6 months and 5 years after transplantation. For the kidney, the same type of approach is being validated.

Since the discovery of acellular DNA (cfDNA) derived from the donor (cfDNA) in the recipient's blood and urine, the clinical interest of cfDNA in the field of transplantation has been growing rapidly.

Today, lung transplantation is an established therapy for patients with advanced lung diseases. Although survival after lung transplantation has improved statistically over the past decade, there are still complications such as:

Complications related to ischemia-reperfusion during the transplantation procedure, defined as primary graft dysfunction (PGD). This complication is the leading cause of death in the first month after lung transplantation (LT);

Acute rejection, which occurs in 33% of recipients in the first year after transplantation. Young recipients have a higher acute rejection rate, around 36%;

Infectious complications related to both immunosuppression and direct interface between lung and external environment;

Chronic rejection, which affects 49% and 76% of recipients after 5 and 10 years, respectively.

The early stages of rejection are diagnosed by transbronchial lung biopsy after bronchoscopy which is very sensitive and specific. However, this technique is expensive, invasive and has limited predictive value. Non-invasive detection of rejects therefore appears of interest, particularly in the case of infra-clinical rejects, which are currently only detectable from biopsies.

The identification of non-invasive markers that predict complications in lung transplantation has become a real challenge.

In comparison to molecular gene expression signatures that predict specific organ rejection, the quantification of the donor's cfDNA can be a universal marker for any type of solid organ transplantation. Persistent increase or high levels of circulating DNA may indicate an acute biopsy-confirmed rejection in renal, pancreatic or cardiac transplant patients. With regard to liver transplantation, the cfDNA level increases in the case of rejection but also in cases of stress, inflammation and with the number of transfusions.

In 2015, De Vlaminck et al. conducted a prospective study on 51 lung transplant patients (398 samples). The circulating DNA level of the donor is estimated in the recipient by the technique of real-time amplification of SNP polymorphisms. The quantification of the donor's cfDNA was significantly higher in the "moderate" or "severe acute cellular rejection" group compared to the "stable" group. In 2017, Zou et al. confirmed these data in 18 lung transplant recipients by detecting the donor's cfDNA by amplifying HLA polymorphisms by digital PCR. Despite all these promising results, routine analysis is not yet effective because the artifactual variability induced by pre-analytical processes is neglected, in particular the cfDNA extraction steps or the coefficients of variation are close to 20%.

Apart from the lung, all transplants can be monitored for rejection: heart, kidney, bone marrow, etc.

The process of the invention advantageously has two applications in this field of transplantation:

1—Monitor the Occurrence of Graft Rejection:

Analysis of cfDNA fluctuations to detect and monitor the occurrence of graft rejection by quantifying circulating DNA released by cell death/lysis of the organ or transplanted cells (donor). The extraction technique according to the invention, IDXtract (ID-Solutions, France), makes it possible to be free from the constraints previously stated, thanks to the addition to the plasma to be extracted of calibrated exogenous DNA: ICE (non-human sequence). The ICE fragment undergoes the extraction steps and ensures the efficiency of the extraction. The qPCR/dPCR kit according to the invention, IDQuant (ID-Solutions, France), makes it possible to co-amplify exogenous ICE DNA with one or more human genome sequences. It is possible to determine the amount of cfDNA and ICE for the same test sample and to calculate the value of the cfDNA/ICE ratio and express it per ml of plasma (cfDNA/ICE/ml plasma=Grewis). The variation in Grewis over time for the same subject of interest ensures that fluctuations in cfDNA of physiological/pathological origin can be monitored longitudinally without artefacts. Thus, the variation in total cfDNA, detected by real-time quantitative PCR or digital PCR, can reflect a rejection process;

2—Monitor Changes in the Concentration of "Donor" DNA:

The detection/quantification of a donor's DNA signature from cfDNA by ddPCR concomitant with the measurement of Grewis and/or the exogenous ICE sequence makes it possible to monitor changes in the "donor" DNA concentration between the different liquid biopsies performed longitudinally. The results are normalized to the ICE fragment (added to the plasma before cfDNA extraction) calibrated by dPCR, expressed per ml of plasma and/or Grewis. Sequence variations in donor DNA or chimerism make it possible, for example, to monitor the increase over time of these sequences, which may be directly or indirectly related to acute or sub-clinical rejection. It is possible, for example, to:

Detect the increase in the amount of circulating DNA from the donor which can signal an acute rejection event regardless of the type of organ transplantation.

Define a decision-making threshold value for change in therapeutic practice

See an interest as biomarkers of organ integrity (Kanzow P et al., Transplantation 2014) with standardized longitudinal monitoring.

Diagnosis of a Pathological Condition

In comparison with mean cfDNA amount values obtained in reference subjects (e.g. healthy subjects: n=24 subjects, mean=9.38 ng/ml plasma±4.47 ng/ml, median=8.94 ng/ml, min=3.21 ng/ml, max=23.38 ng/ml), the obtaining of "abnormal" Grewis values, meaning values higher or even much higher than the values of the reference subjects, signals a pathological condition, it is possible to refer the patient to more specialized consultations to refine the diagnosis.

The invention further relates to the use of at least a first exogenous DNA fragment of 50-2000 base pairs, preferably 50-200 base pairs, preferably 60-160 base pairs, more preferably 70-150 base pairs and better 80-140 base pairs (ICE), for use in standardizing a method for extracting and quantifying cell-free DNA and/or in a method for analyzing fluctuations in cell-free DNA in a subject of interest over time by measuring the ratio (Grewis) of the copy number of cell-free DNA to the copy number of the first exogenous DNA fragment of 50-2000 base pairs, preferably 50-200 base pairs, preferably 60-160 base pairs, more preferably 70-150 base pairs and better 80-140 base pairs (ICE).

Kits and Sets for Extraction, Amplification-Quantification of Circulating DNA

Another object of the invention is a kit or set for extracting cell-free DNA from a biological fluid sample from a subject of interest, comprising:

(i) At least a first exogenous DNA fragment of 50-2000 base pairs, preferably 50-200 base pairs, preferably 60-160 base pairs, more preferably 70-150 base pairs and better 80-140 base pairs (ICE);

(ii) Buffers and enzymes, in particular a cell-free DNA proteolysis buffer, proteolysis enzyme, binding buffer, wash buffer, and elution buffer, (iii) Devices for isolating cell-free DNA, in particular silica membrane extraction columns and advantageously extraction columns surmounted by loading accessories, preferably funnels, (iv) Multi-well plates, in particular 24-well DeepWell 25 ml plates (v) Screw-cap tubes, preferably 1.5 ml, and (vi) A user manual, said exogenous ICE DNA fragment being provided in said kit or provided separately to said kit, forming an extraction set.

According to a particular embodiment, the circulating DNA extraction kit according to the invention comprises:

(i) At least a first non-human exogenous DNA fragment of 300 base pairs and optionally a second non-human exogenous DNA fragment of 110 base pairs, both of which being DNA sequences encoding the precursor of an aggregating serine protease from *Cerastes cerastes*

(ii) Buffers and enzymes: a proteolysis buffer advantageously supplemented with bovine serum albumin (BSA) and/or purified pork gelatin (Prionex®), a lysis enzyme, preferably proteinase K, a binding buffer, a wash buffer, an elution buffer,
(iii) Silica membrane extraction columns, 24-well DeepWell 25 ml plates, funnels, 1.5 ml screw-cap tubes and
(iv) A user manual.

According to another particular and preferred embodiment, the circulating DNA extraction kit according to the invention comprises:

(i) At least a first non-human exogenous DNA fragment (ICE) of 110 base pairs encoding the precursor of an aggregating serine protease from *Cerastes cerastes*
(ii) Buffers and enzymes: a proteolysis buffer advantageously supplemented with bovine serum albumin (BSA) and/or purified pork gelatin (Prionex®), a lysis enzyme, preferably proteinase K, a binding buffer, a wash buffer, an elution buffer,
(iii) Silica membrane extraction columns, 24-well DeepWell 25 ml plates, funnels, 1.5 ml screw-cap tubes and
(iv) A user manual.

According to a particular embodiment, a kit according to the invention may be characterized by the parameters defined in Table 1 below:

TABLE 1

| | |
|---|---|
| Technology | Silica membrane technology |
| Format | Midi columns with removable funnel |
| Sample | 1 to 10 ml of plasma, in particular 1 to 5 ml of plasma |
| Blood collection tubes | EDTA, Cell-free DNA BCT ® (Streck), Roche |
| Fragment size | ≥50 bp |
| Yield | From 1 to 1000 ng |
| Elution volume before concentration | 100-200 µl |
| Elution volume after concentration | 50 µl |
| Preparation time | 2 h 15 min per 24 preparations |

According to a particular embodiment, it will be a kit for extracting cell-free DNA from blood plasma. This kit allows the purification of cell-free DNA from a volume of up to 100 ml of plasma, notably 10 ml of plasma, in particular 5 ml of plasma.

The kit contains Midi columns, preferably with loading accessories for said columns, preferably funnels allowing the entire sample/extraction solution mixture to be loaded at once and allowing 1 to 24 samples to be processed in parallel.

The binding, washing, drying and eluting of cell-free DNA is done with a vacuum chamber device, and column supports (Starter S and Midi)

Extraction is done advantageously without entraining DNA or RNA (formation of a complex with the DNA in order to facilitate its isolation). Indeed, these entraining DNA or RNA cause an overestimation of cell-free DNA concentrations when total, double or single strand DNA quantification techniques are used.

According to a particular embodiment, the cell-free DNA extraction kit according to the invention is used in combination with a cell-free DNA amplification and quantification kit, supplied together or separately.

According to a first embodiment, the cell-free DNA extraction kit according to the invention and the cell-free DNA amplification and quantification kit are packaged together.

According to a first embodiment, the cell-free DNA extraction kit according to the invention and the cell-free DNA amplification and quantification kit are packaged separately.

The cell-free DNA amplification and quantification kit will generally comprise at least:
(i) specific sense and antisense primers for the cell-free DNA of the subject of interest and for the exogenous DNA fragment(s) as defined in the invention, for the amplification step,
(ii) labeled probes for the cell-free DNA of the subject of interest and for the exogenous DNA fragment(s) as defined in the invention for the detection and quantification step,
(iii) reaction buffers,
(iv) multi-well plates and
(v) a user manual.

FIGURES

FIG. 1: Graphical representation of variability of circulating DNA after extraction and of the normalization of the extraction and the quantification through the use of an exogenous ICE fragment according to the process of the invention;

FIG. 2: Graphical representation of the concomitant analysis of genomic abnormalities (EGFR mutations) and the exogenous ICE sequence and/or Grewis;

FIG. 3: Graphical representation of the concomitant analysis of genomic abnormalities (EGFR mutations) and Grewis.

The present invention will be detailed in the following illustrative and non-limiting examples.

EXAMPLES

Plasma samples are prepared according to the following protocol:
Plasma is prepared from whole blood collected on a BCT® (Streck) or Cell-Free DNA Collection Tube (Roche) or EDTA tube. For EDTA tubes, the plasma must be prepared within 4 hours of the blood test;
The tubes are centrifuged at 1600×g for 10 minutes at room temperature;
The supernatant (corresponding to the plasma) is collected and then transferred into a 15 ml conical tube;
The recovered plasma is centrifuged at 4500 g for 10 minutes at room temperature;
The plasma is transferred to a conical tube and the volume is measured;
The plasma volume is adjusted to the higher milliliter if necessary with phosphate buffer and then transferred to a 50 ml tube or placed in a 25 ml DeepWell.

Preferably, the plasma samples are prepared from a subject of interest likely to release cfDNA, i.e. a subject suffering from or likely to develop a cancer or a clinical condition selected from stroke or myocardial infarction, acute renal failure, hepatic cytolysis, trauma, surgery, graft rejection, or subject to intensive muscle exercise, or subject to medical treatment such as biopsy, surgery, radiotherapy, chemotherapy, immunotherapy, or active principle (chemical or biological).

Example 1: Standardized Extraction of Circulating DNA from a Plasma Sample 1.1 Plasma Proteolysis Proteolysis of the plasma samples as prepared above is performed according to the following protocol:
In addition to the plasma samples, a control sample CQI (lyophilized culture medium of human lung cell line NCI-H1975, CRL-5908) also known as extraction quality control according to the invention is used to control the extraction quality;
To each plasma sample and control sample, 30 µl of liquid proteinase K is added per ml of sample;
Next, to each sample per ml (plasma and control sample) are added 20,000 copies of the first exogenous DNA fragment of 300 base pairs (ICE) represented by SEQ ID NO: 1 described below and 20,000 copies of the second exogenous DNA fragment of 110 base pairs (LED) represented by SEQ ID NO: 2 described below, both of which being DNA sequences encoding the precursor of an aggregating serine protease from *Cerastes cerastes*;
The samples are briefly vortexed and then incubated for 5 minutes at room temperature;
400 µl of lysis buffer (LYS) per ml of plasma or control is then added to each sample;
The samples are briefly vortexed and incubated at 56° C. for 30 minutes with shaking or 1 hour for Streck tubes.

SEQ ID NO: 1:
CCTAATGACACTTATCCCAAAGTCCCTCATTGTGCTAACATTAACATACT

TGAGCATTCGCTGTGTGAAAGAGCTTACAATGATCTTTCGGCGAGTAGCA

GAACATTGTGTGCAGGTATCGAAAAAGGAGGCATAGATACATGTAAGGGT

GACTCTGGGGGACCCCTCATCTGTAATGGACAAATCCAGGGCATTGTATC

TTGGGGAGATGAAGTTTGTGGTAAACCTAATAAGCCTGGCGTCTATACCA

AGGTCTTTGATTATACTGACTGGATCCGGAACATTATTGCAGGAAATACA

SEQ ID NO: 2:
GCTGAACAAACCAGTTAACAACAGTACACACATCGCGCCTCTCAGCTTGC

CTTCCAGTCCTCCCAGTGTGGGCTCAGATTGCCGTATTATGGGATGGGGC

ACAATCACAT 1.2 Isolation of Circulating DNA on the Columns:

The isolation and binding of circulating DNA on the columns is performed according to the following protocol:
During lysis incubation, 1 ml of silica membrane activation buffer (ACTIVB) is applied in each MIDI column, incubated for 1 minute and vacuumed is applied at −0.4 bar for 1 minute;
2 ml of binding buffer (BB) per ml of plasma is added to each lysed sample;
The contents of the tube are mixed by drawing/expelling at least 5 times;
The funnels are placed on each column;
The lysed sample mixture is applied to the MIDI columns;
Finally, the vacuum is applied at −0.4 bar for 5 minutes, making sure that all the lysate has passed through the column.

1.3 Washing the Membrane:

The membrane washing step is performed according to the following protocol:

4 ml of wash buffer Wash 1 is added to each column, which is then incubated for 1 minute;

The vacuum is applied at −0.4 bar for 5 minutes;

2 ml of wash buffer Wash 2 is added to each column, which is then incubated for 1 minute;

The vacuum is applied at −0.4 bar for 2 minutes;

2 ml of buffer Wash 2 is added to each column, which is then incubated for 1 minute;

Finally, the vacuum is applied at −0.4 bar for 2 minutes.

1.4 Elution of Circulating DNA

Before eluting the circulating DNA, the vacuum, at least −0.6 bar, is applied for 10 minutes to completely dry the membrane of any trace of ethanol.

Elution of circulating DNA is then performed according to the following protocol:

150 µl of elution buffer, supplemented with 1% Prionex® (ELU) just before use and previously heated to 70° C., is then added to each column;

The columns are incubated for 5 minutes at room temperature;

The vacuum is applied at −0.5 bar for 30 seconds;

Finally, the vacuum is applied again at −0.5 bar for 10 sec 1.5 Optional Concentration of Circulating DNA Samples for Single Analysis Concentration of the circulating DNA is performed according to the following protocol:

All eluates are loaded into the ultrafiltration plate;

The vacuum is applied at −0.5 bar for 10 minutes (complete passage of the volume);

50 µl of elution buffer is added to each well containing the samples;

The plates are shaken for 5 minutes at room temperature;

Finally, the samples are transferred to a new, pre-labeled tube.

1.6 Storage and/or Preservation of Extracted Circulating DNA

The circulating DNA obtained must be stored at 5° C.±3° C. if ddPCR or qPCR is performed following, otherwise the circulating DNA must be stored at −80° C. for longer storage.

According to an alternative embodiment, to each sample per ml (plasma and control sample) are added between 10,000 and 20,000 copies of a first exogenous DNA fragment of 110 base pairs (ICE) represented by SEQ ID NO: 2 encoding the precursor of an aggregating serine protease from *Cerastes cerastes* and playing the role of both ICE and LED.

Example 2: Detection and Quantification of Circulating DNA with Internal Control (ICE)-300 Base Pair Fragment The detection of the circulating DNA extracted in example 1 and its quantification is performed by digital droplet PCR (ddPCR) according to the following protocol, for a reaction volume of 20 µl/sample:

10 µl of ddPCR Supermix for probes (no dUTP) (Bio-Rad) is added 0.1 µl of a sense primer directed against the first exogenous DNA fragment for the exogenous internal control ICE (TGG-ACA-AGG-ACA-TCA-TGC-TGA-T corresponding to SEQ ID NO: 3) is added at 100 µM;

0.1 µl of an antisense primer directed against the first exogenous DNA fragment for the exogenous internal control ICE (GAC-TGG-AAG-GCA-AGC-TGA-GA corresponding to SEQ ID NO: 4) is added at 100 µM;

0.06 µl of HEX and BHQ1 labeled probe directed against the exogenous internal control ICE (AAC-CAG-TTA-ACA-ACA-GTA-CAC-ACA-TCG-CGC corresponding to SEQ ID NO: 5) is added at 100 µM;

0.1 µl of a sense primer directed against the human RPP-30 gene (GAT-TTG-GAC-CTG-CGA-GCG corresponding to SEQ ID NO: 6) is added at 100 µM;

0.1 µl of an antisense primer directed against the human RPP-30 gene (GAG-CGG-CTG-TCT-CCA-CAA-GT corresponding to SEQ ID NO: 7) is added at 100 µM;

0.06 µl of FAM and MGB labeled probe directed against the human RPP-30 gene (CTG-ACC-TGA-AGG-CTC-T corresponding to SEQ ID NO: 8) is added at 100 µM;

1.48 µl of molecular biology grade $H_2O$ is added;

8 µl of the extracted DNA (extracted circulating DNA and exogenous DNA fragment) is added;

the mixture is homogenized and loaded into a well of a DG8™ cartridge (Bio-Rad)

70 µl of oil for droplet generation is added to the DG8™ cartridge (Bio-Rad)

the DG8™ gasket (Bio-Rad) is installed and droplets are generated using the Bio-Rad Droplet Generator;

the sample is transferred to a 96-well plate, sealed and a finite-time PCR is performed according to the program below:

Step 1: 95° C. 10 min
Step 2: 94° C. 30 sec
Step 3: 60° C. 1 min
Repeat steps 2 and 3 40 times
Step 4: 98° C. 10 minutes
Step 5: 12° C. 1 sec At the end of the PCR, the 96-well plate is transferred to the Bio-Rad droplet reader and the droplets are read.

The same amplification and quantification step is performed for the DNA extracted from the plasma sample and for the DNA extracted from the control sample.

The results obtained for the RPP30 gene represent the extracted circulating DNA copy number. The results obtained for the extracted exogenous DNA fragment (ICE) represent the extracted ICE copy number.

The Grewis calculation is done by dividing the value obtained for RPP30 by the value obtained for ICE. This value serves as a reference value that can be compared between each extraction for the same subject and thus determine the variation in the amount of free DNA of that subject over time.

A ratio (Grewis) representative of the amount of circulating DNA in the sample from the subject of interest is obtained.

Example 3: Detection and Quantification of Circulating DNA with Additional Control of the (LED)-300 Base Pair ICE Fragment and 110 Base Pair LED Fragment Size Profile The detection of the circulating DNA extracted in example 1 and its quantification is performed by digital droplet PCR (ddPCR) according to the following protocol, for a reaction volume of 20 µl/sample:

10 µl of ddPCR Supermix for probes (no dUTP) (Bio-Rad) is added 0.1 µl of a sense primer directed against the first exogenous DNA fragment for the exogenous internal control ICE (TGG-ACA-AGG-ACA-TCA-TGC-TGA-T corresponding to SEQ ID NO: 3) is added at 100 μM;

0.1 μl of an antisense primer directed against the first exogenous DNA fragment for the exogenous internal control ICE (GAC-TGG-AAG-GCA-AGC-TGA-GA corresponding to SEQ ID NO: 4) is added at 100 μM;

0.06 μl of HEX and BHQ1 labeled probe directed against the exogenous internal control ICE (AAC-CAG-TTA-ACA-ACA-GTA-CAC-ACA-TCG-CGC corresponding to SEQ ID NO: 5) is added at 100 μM;

0.1 μl of a sense primer directed against the second exogenous DNA fragment for extraction control of small LED fragments (ATG-ACA-CTT-ATC-CCA-AAG-TCC-CTC corresponding to SEQ ID NO: 9) is added at 100 μM;

0.1 μl of an antisense primer directed against the second exogenous DNA fragment for extraction control of small LED fragments (CAA-TGT-TCT-GCT-ACT-CGC-CGA corresponding to SEQ ID NO: 10) is added at 100 μM;

0.06 μl of FAM and MGB labeled probe directed against the exogenous internal control LED (CAT-ACT-TGA-GCA-TTC-GCT-GT corresponding to SEQ ID NO: 11) is added at 100 μM;

1.48 μl of molecular biology grade H$_2$O is added;

8 μl of the extracted DNA (extracted circulating DNA and second exogenous DNA fragment) is added;

the mixture is homogenized and loaded into a well of a DG8™ cartridge (Bio-Rad)

70 μl of oil for droplet generation is added to the DG8™ cartridge (Bio-Rad)

the DG8™ gasket (Bio-Rad) is installed and the droplets are generated using the Bio-Rad Droplet Generator;

the sample is transferred to a 96-well plate, sealed and a finite-time PCR is performed according to the program below:

Step 1: 95° C. 10 min
Step 2: 94° C. 30 sec
Step 3: 60° C. 1 min
Repeat steps 2 and 3 40 times
Step 4: 98° C. 10 minutes
Step 5: 12° C. 1 sec At the end of the PCR, the 96-well plate is transferred to the Bio-Rad droplet reader and the droplets are read.

The same extraction, amplification and quantification steps are performed for DNA extracted from the plasma sample and for DNA extracted from the control sample.

The results obtained for the extracted exogenous DNA fragment (ICE) represent the extracted ICE copy number. The results obtained for the second extracted exogenous DNA fragment (LED) represent the extracted LED copy number.

The calculation of the small fragment extraction control is performed by dividing the value obtained for ICE by the value obtained for LED.

ICE/LED ratios close to 1 are obtained, which must remain stable from one extraction to another. If this ratio increases, it means that the DNA of small size has not been extracted correctly, and that the results obtained on the quantification of circulating DNA are biased.

Amplification and quantification can also be performed by simultaneously using the three targets (circulating DNA, ICE and LED) as described in examples 2 and 3 above, respectively.

Example 4: Detection and Quantification of Circulating DNA with 110 Base Pair Internal Control (ICE) Also Playing the Role of LED Example 2 above is repeated using, as exogenous ICE fragment, the 110 base pair fragment corresponding to sequence SEQ ID NO: 2.

The detection of the circulating DNA extracted in example 1 and its quantification is performed by digital droplet PCR (ddPCR) according to the following protocol, for a reaction volume of 20 μl/sample:

10 μl of ddPCR Supermix for probes (no dUTP) (Bio-Rad) is added 0.1 μl of a sense primer directed against the exogenous DNA fragment for the exogenous internal control ICE (ATG-ACA-CTT-ATC-CCA-AAG-TCC-CTC corresponding to SEQ ID NO: 9) is added at 100 μM;

0.1 μl of an antisense primer directed against the exogenous DNA fragment for the exogenous internal control ICE (CAA-TGT-TCT-GCT-ACT-CGC-CGA corresponding to SEQ ID NO: 10) is added at 100 μM;

0.06 μl of FAM and MGB labeled probe directed against the exogenous internal control ICE (CAT-ACT-TGA-GCA-TTC-GCT-GT corresponding to SEQ ID NO: 11) is added at 100 μM;

0.1 μl of a sense primer directed against the human RPP-30 gene (GAT-TTG-GAC-CTG-CGA-GCG corresponding to SEQ ID NO: 6) is added at 100 μM;

0.1 μl of an antisense primer directed against the human RPP-30 gene (GAG-CGG-CTG-TCT-CCA-CAA-GT corresponding to SEQ ID NO: 7) is added at 100 μM;

0.06 μl of FAM and MGB labeled probe directed against the human RPP-30 gene (CTG-ACC-TGA-AGG-CTC-T corresponding to SEQ ID NO: 8) is added at 100 μM;

1.48 μl of molecular biology grade H$_2$O is added;

8 μl of the extracted DNA (extracted circulating DNA and exogenous DNA fragment) is added;

the mixture is homogenized and loaded into a well of a DG8™ cartridge (Bio-Rad)

70 μl of oil for droplet generation is added to the DG8™ cartridge (Bio-Rad)

the DG8™ gasket (Bio-Rad) is installed and the droplets are generated using the Bio-Rad Droplet Generator;

the sample is transferred to a 96-well plate, sealed and a finite-time PCR is performed according to the program below:

Step 1: 95° C. 10 min
Step 2: 94° C. 30 sec
Step 3: 60° C. 1 min
Repeat steps 2 and 3 40 times
Step 4: 98° C. 10 minutes
Step 5: 12° C. 1 sec At the end of the PCR, the 96-well plate is transferred to the Bio-Rad droplet reader and the droplets are read.

The same amplification and quantification step is performed for the DNA extracted from the plasma sample and for the DNA extracted from the control sample.

The results obtained for the RPP30 gene represent the extracted circulating DNA copy number. The results obtained for the extracted exogenous DNA fragment (ICE) represent the extracted ICE copy number.

The Grewis calculation is done by dividing the value obtained for RPP30 by the value obtained for ICE. This value serves as a reference value that can be compared between each extraction for the same subject and thus determine the variation in the amount of free DNA of that subject over time.

A ratio (Grewis) representative of the amount of circulating DNA in the sample from the subject of interest is obtained.

FIG. 1a shows an intra-test variability of cfDNA after extraction, in the absence of exogenous ICE DNA fragment. In the presence of an exogenous ICE fragment, calibrated by ddPCR and added to the plasma before extraction, a homogeneity of the value of the genomic DNA to ICE ratio (Grewis) is observed in FIG. 1b. The ICE fragment is used to normalize the extraction and the quantification. The variation in Grewis alone over time for the same subject of interest ensures that fluctuations in cfDNA of physiological/pathological origin can be monitored longitudinally without artefacts.

Example 5: Process for Monitoring the Physiological State of a Subject of Interest with Concomitant Investigation of EGFR Mutation in Non-Small Cell Lung Cancers Used in combination with a cfDNA extraction and detection kit as described in examples 1 and 4 is an IDEGFR kit for the detection and quantification by digital PCR of EGFR mutations involved in patient stratification for targeted therapies using tyrosine kinase inhibitors and associated resistance.

This is a multiplex quantification system that allows, for each sample, the simultaneous amplification in two reactions of activating mutations (L858R and Del19—$1^{st}$ reaction) and resistance mutations (T790M and C797S—$2^{nd}$ reaction). Activating mutations of the gene encoding EGFR appear mainly in non-small cell lung cancer (NSCLC) and cause constitutive activation of EGFR protein kinase activity, thus contributing to the oncogenic process. The most common mutations include a variety of deletions at exon 19 and an L858R substitution in exon 21. These mutations constitute 85% of the EGFR mutations observed in NSCLC. The T790M and C797S mutations represent two mutations described as conferring resistance to the targeted therapies erlotinib and osimertinib, respectively.

The IDEGFR kit contains the following reagents:
- A target positive control (TPC-IDEGFR) comprising a mixture of synthetic DNA carrying the different mutations and calibrated to the concentration mentioned in the associated quality control sheet;
- An amplification reaction mixture (ARM-IDEGFR sensi) containing Taq polymerase and oligonucleotides for the detection of EGFR (FAM/HEX) and L858R (FAM) mutations and Exon 19 (HEX) deletion;
- An amplification reaction mixture (ARM-IDEGFR resist) containing Taq polymerase and oligonucleotides for the detection of EGFR (FAM low) and T790M (FAM high) and C797S (HEX) mutations;
- A negative extraction control (NEC) prepared and extracted in the same manner as the samples to be tested but not containing a sample (replaced by PBS);
- A negative amplification control (NAC) corresponding to the deposition of 13 µl of amplification reaction mixture and 8 µl of Nuclease-free water.

Circulating DNA is extracted from the samples according to the protocol described in example 4, before being amplified.

The amplification reaction by finite-time PCR (Bio-Rad QX200 digital PCR) is performed in each well in the presence of 13 µl of ARM-IDEGFR (Sensi or Resist) for each sample and for positive and negative controls. The following are added to each reaction mix:
- 8 µl of DNA extracted from each sample to be analyzed
- 8 µl of TPC-IDEGFR DNA
- 8 µl of NEC extract
- 8 µl of nuclease-free water (NAC).

The amplification phase is performed according to the following program:
1) Polymerase activation (10 min at 95° C., 1 cycle);
2) DNA denaturation/elongation (15 seconds at 95° C. and 60 seconds at 60° C., 40 cycles);
3) Droplet consolidation (10 minutes at 98° C., 1 cycle);
4) Cooling (infinite time at 12° C., 1 cycle).

The results are analyzed using the QuantaSoft™ Analysis Pro software.

A mutation is considered positive if the positive droplet value is greater than or equal to 2.

A mutation is considered undetected if its value is zero or less than 2 positive droplets.

Figure 1A:
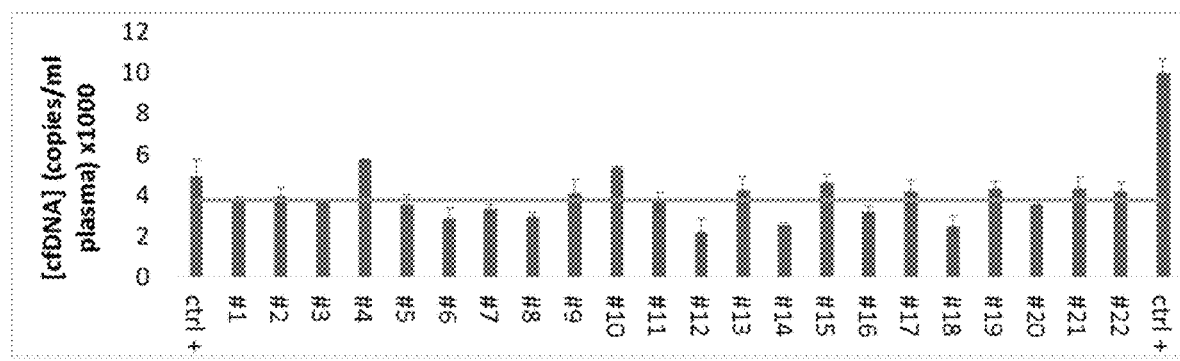
Figure 1B:
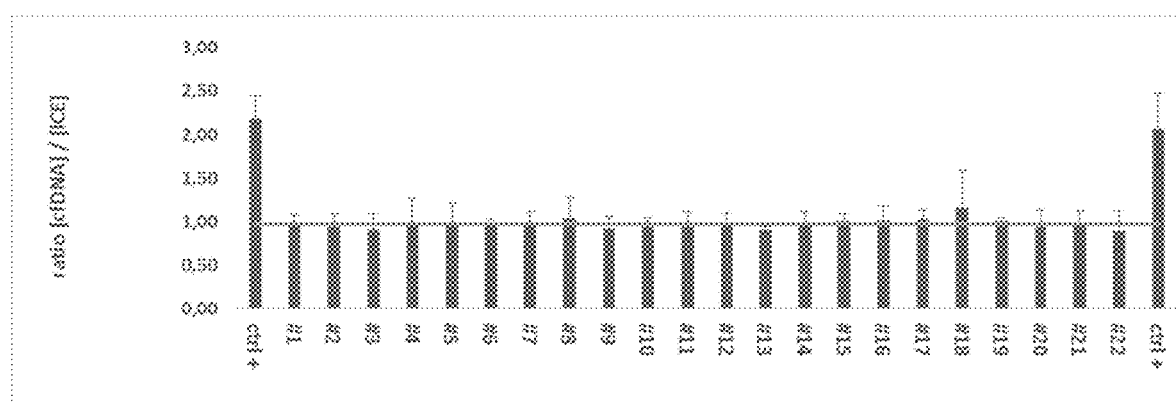
Figure 2A:
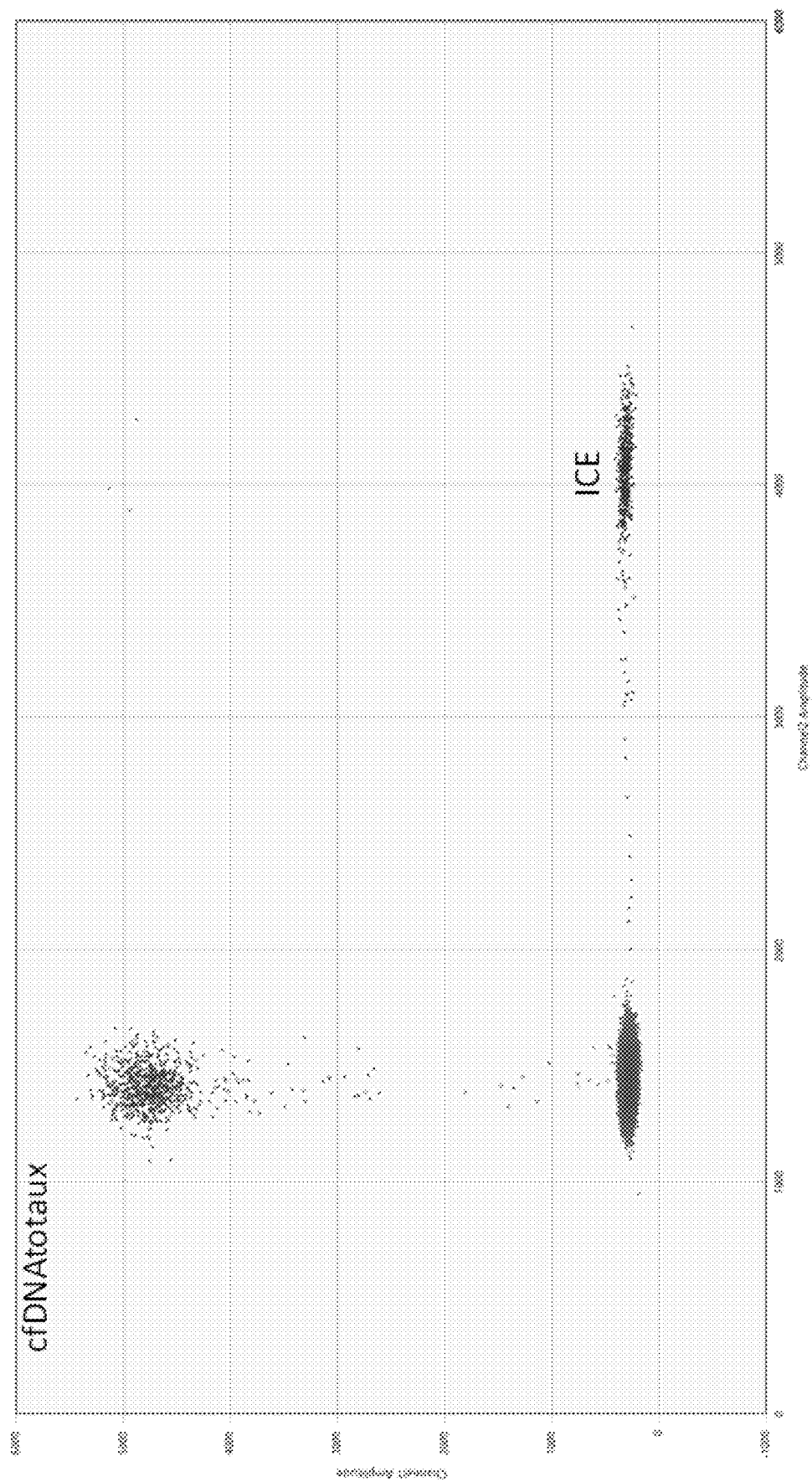
FIG. 2a shows the results of the co-amplification of cfDNA (RPP30) and ICE by dPCR.
Figure 2B:
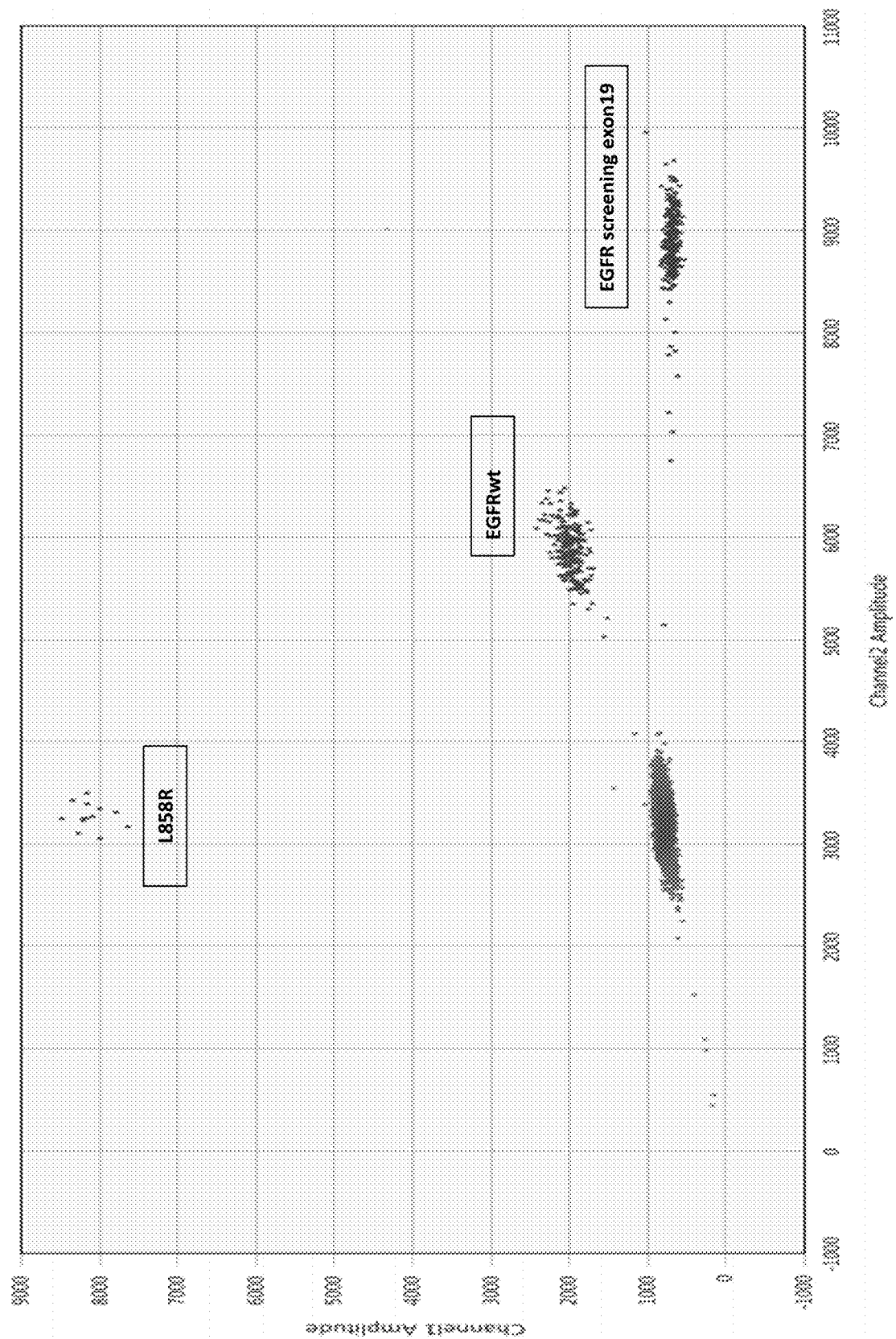
FIG. 2b shows the analysis of EGFR mutations by the IDEGFR tube mutations ARM-IDEGFR sensi kit.
Figure 3A:
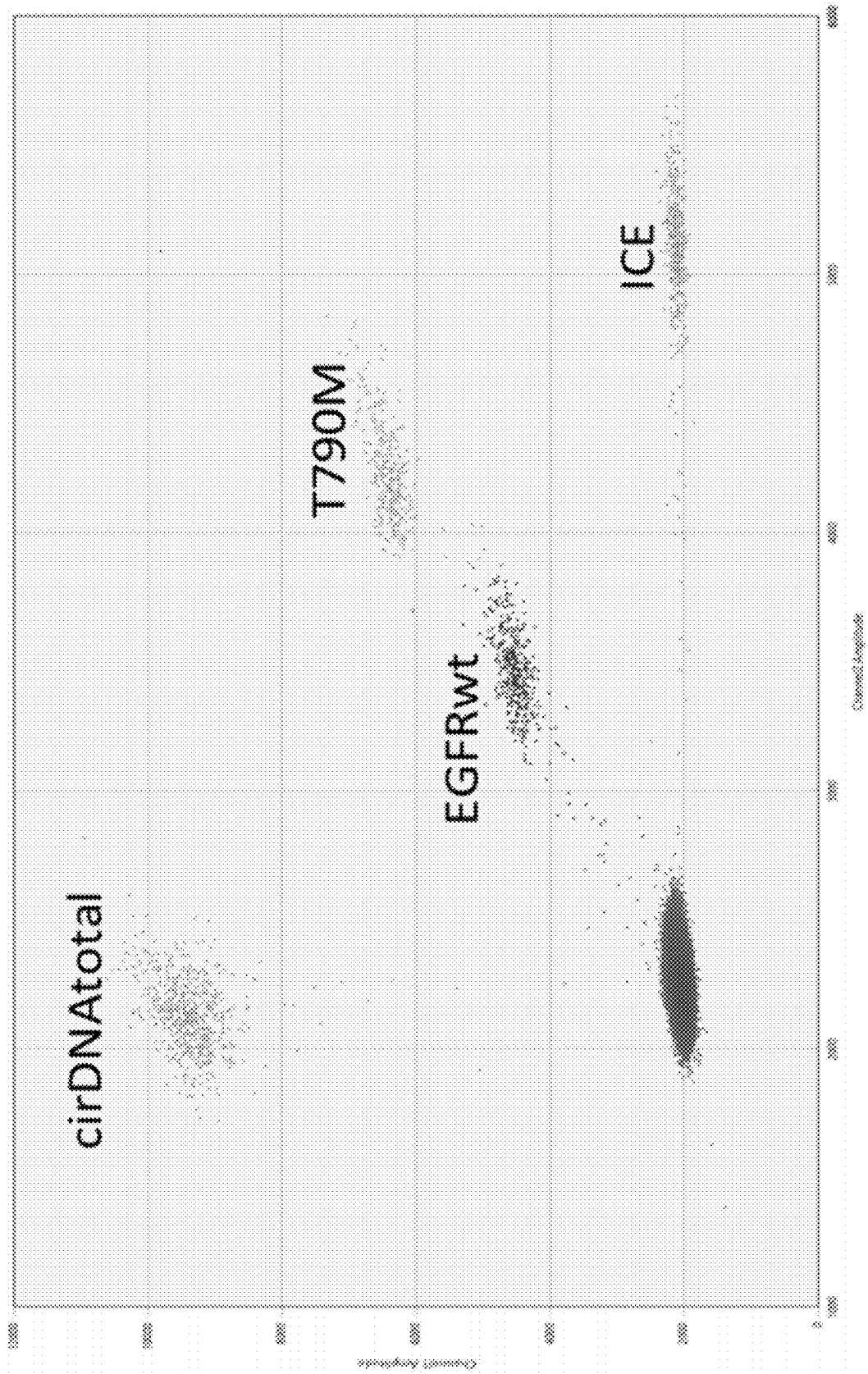
FIG. 3a illustrates the analysis of EGFR mutations by the IDEGFR tube mutations ARM-IDEGFR resist kit with ICE co-amplification.
Figure 3B:
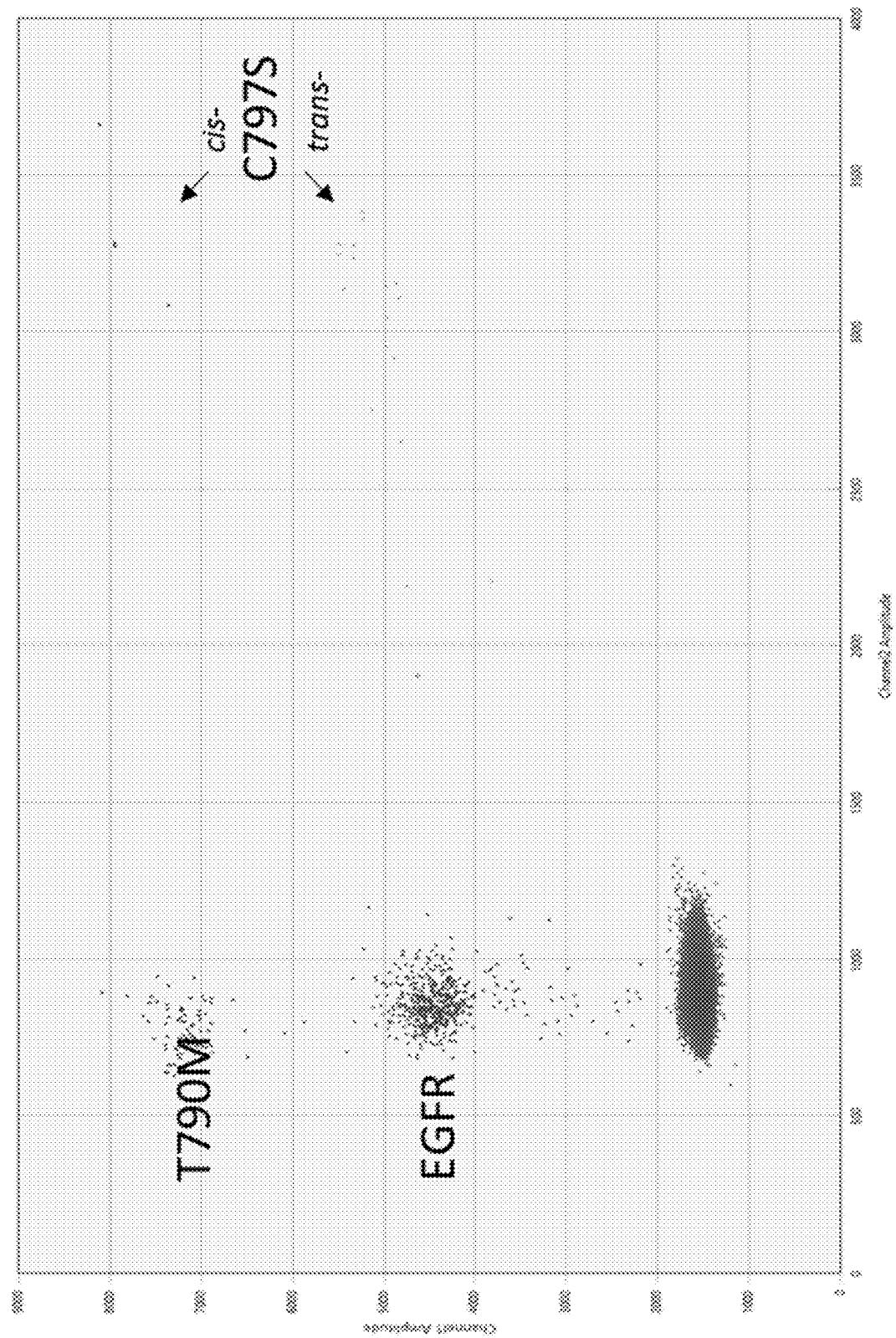
FIG. 3b illustrates the analysis of EGFR mutations by the IDEGFR tube mutations ARM-IDEGFR resist kit.

The detection/quantification of genomic abnormalities concomitant with the measurement of Grewis and/or the exogenous ICE sequence makes it possible to monitor changes in the concentration of mutated DNA between the different liquid biopsies performed longitudinally.

Based on the fluctuation in the % mutant normalized by Grewis, the targeted treatment is adapted.

Example 6: Process for Detecting/Quantifying a Donor's DNA Signature from cfDNA by ddPCR Concomitant with the Measurement of Grewis and/or the Exogenous ICE Sequence In combination with a cfDNA extraction and detection kit as described in examples 1 and 4, a digital PCR detection and quantification kit for donor DNA (after transplantation) is used. The protocol is similar to the protocol described in example 5 for mutated DNA, except that the probes used are specific to donor DNA rather than mutated DNA.

The variation over time of Grewis is due, in a pathological state, to a fluctuation in physiological/pathological cfDNA:
- An increase in the ratio indicates graft rejection;
- A decrease in the ratio indicates that the graft has taken;
- A steady state indicates that the graft is intact.

The detection/quantification of 'donor' DNA concomitant with the measurement of Grewis and/or the exogenous ICE sequence also makes it possible to monitor changes in the concentration of "donor" DNA between the different liquid biopsies performed longitudinally.

Example 7: Use of the Measurement of Grewis and/or of the Exogenous ICE Sequence in an Analytical Process of Genomic Analysis ('Hub' Role)

A cfDNA extraction, detection and amplification kit is used according to the protocols described in examples 1 and 4, in the presence of an ICE fragment.

The variation in Grewis due, in a pathological state, to a physiological/pathological cfDNA fluctuation can be used to decide whether it is appropriate to carry out a subsequent genomic analysis:
- No fluctuation or increase in Grewis: genomic analysis is pointless;
- If Grewis increases: genomic analysis is useful; cfDNA is concentrated at the end of the extraction step before amplification or any other genomic analysis with targeted or non-targeted sequencing technique (NGS and others).

Example 8: In Vitro Process to Assist in the Diagnosis of a Pathological Condition In comparison with average values obtained on healthy subjects and a persistence of "abnormal" Grewis values, it is possible to direct the subject of interest towards more specialized consultations to refine the diagnosis:
- Decrease in the ratio (Grewis): response to medical treatment, whatever its nature (surgery, active principle, etc.), suggesting the efficacy of the treatment and therefore its maintenance;
- Increase in the ratio (Grewis): insufficient or no response to treatment, suggesting a change in treatment;
- Steady state of the ratio (Grewis): the treatment is still effective.

The invention claimed is:

1. Process for quantifying a first sample target nucleic acid sequence within cell-free DNA from a biological fluid sample from a subject, wherein the subject is or will be undergoing medical treatment; is or will be recovering from a trauma or surgery; or is affected by, is likely to have, or is at risk of-developing a clinical condition selected from the group consisting of cancer, stroke, myocardial infarction, acute renal failure, and hepatic cytolysis, said process comprising:

(i) collecting a volume of a biological fluid sample from the subject, wherein the biological fluid sample comprises cell-free DNA from the subject, said cell-free DNA comprising a first sample target nucleic acid sequence;

(ii) adding to the biological fluid sample a fixed amount of a first exogenous DNA, wherein the fixed amount is between 1 fg to 2 ng, wherein the first exogenous DNA comprises DNA fragments 110-140 nucleic acid bases in length comprising at least 110 bases of SEQ ID NO: 2, wherein said DNA fragments comprise a first exogenous target nucleic acid sequence;

(iii) co-extracting the cell-free DNA and the first exogenous DNA from the biological fluid sample;

(iv) co-amplifying, in a single well, the first sample target nucleic acid sequence and the first exogenous target nucleic acid sequence to produce an amplified first sample nucleic acid product and an amplified first exogenous nucleic acid product;

(v) quantifying the amplified first sample nucleic acid product and the amplified first exogenous nucleic acid product and determining a ratio of the quantified amplified first sample nucleic acid product and the amplified first exogenous nucleic acid product; and (vi) determining a quantity per unit volume of the sample target nucleic acid sequence within the biological fluid sample based on the ratio from step (v) and the fixed amount of the first exogenous DNA added in step (ii) and the volume of biological sample tested.

2. A process according to claim 1, wherein the subject is affected by a cancer.

3. A process according to claim 1, wherein the biological fluid sample is selected from the group consisting of whole blood, serum, plasma, urine, saliva, bone marrow effluent, lymph, cerebrospinal fluid, tear fluid, sweat, milk, aqueous humor, synovial fluid, pleural fluid, peritoneal fluid, amniotic fluid, bile, seminal fluid, and expectorations.

4. A process according to claim 3, wherein said biological fluid sample is plasma.

5. A process according to claim 1, wherein the extraction step (iii) comprises the following steps:
(iii1) proteolysis of said biological fluid sample,
(iii2) isolation of the first exogenous DNA along with the cell-free DNA by affinity for a support, and
(iii3) elution from the support of the first exogenous DNA along with the cell-free DNA isolated in step (iii2) in an aqueous phase.

6. A process according to claim 5, wherein the extraction step (iii) further comprises one or more of the following steps:
(iii4) precipitation of the cell-free DNA,
(iii5) concentration of the cell-free DNA, and
(iii6) preservation and/or storage of said cell-free DNA.

7. A process according to claim 1, wherein the sample target nucleic acid sequence comprises a genomic DNA sequence selected from a wild-type DNA sequence and a mutated DNA sequence.

8. A process according to claim 1, wherein said medical treatment is selected from the group consisting of biopsy, surgery, radiotherapy, chemotherapy, immunotherapy, and active principle.

9. A process according to claim 1, wherein said first exogenous DNA comprises DNA fragments 80-140 nucleic acid bases in length.

10. A process according to claim 1, wherein said co-amplifying and/or quantifying steps comprise digital PCR, qPCR, and/or Next Generation Sequencing (NGS).

11. In vitro process for analysis, diagnosis, prognosis, theranosis, or monitoring of changes in a specific physiological state of a subject, wherein the subject is undergoing a medical treatment, is recovering from a trauma or surgery, or is affected by a clinical condition selected from the group consisting of cancer, stroke, myocardial infarction, acute renal failure, and hepatic cytolysis, the process comprising:

(i) collecting a first volume of a first biological fluid sample from the subject at a first time point and collecting a second volume of a second biological fluid sample from the subject at a second time point, wherein the first and second biological fluid samples each comprise cell-free DNA from the subject, said cell-free DNA comprising a sample target nucleic acid sequence, wherein the sample target nucleic acid sequence comprises a genomic DNA sequence selected from a wild-type DNA sequence and a mutated DNA sequence;

(ii) adding to the first and second biological fluid sample a fixed amount of a first exogenous DNA, wherein the fixed amount is between 1 fg to 2 ng, wherein the first exogenous DNA comprises DNA fragments 110-140 nucleic acid bases in length comprising at least 110 bases of SEQ ID NO: 2, wherein said DNA fragments comprise a first exogenous target nucleic acid sequence;

(iii) co-extracting the cell-free DNA and the first exogenous DNA from each of the first and second biological fluid samples;

(iv) for each of the first and second biological fluid samples, using the co-extracted cell-free DNA and the first exogenous DNA from step (iii), co-amplifying, in a single well, the sample target nucleic acid sequence and the first exogenous target nucleic acid sequence to produce an amplified sample nucleic acid product and an amplified first exogenous nucleic acid product for each of the first and second biological fluid samples;

(v) for each of the first and second biological fluid samples, quantifying the amplified sample nucleic acid product and the amplified first exogenous nucleic acid product from step (iv) and determining a ratio of the quantified amplified sample nucleic acid product and the amplified first exogenous nucleic acid product;

(vi) for each of the first and second biological fluid samples, determining a quantity per unit volume of the sample target nucleic acid sequence within the cell-free DNA based on the ratio from step (v) and the fixed amount of first exogenous DNA added in step (ii) and the volume of biological sample tested; and (vii) comparing the quantity of the sample target nucleic acid within the cell-free DNA for the first and second biological fluid samples and performing an analysis, diagnosis, prognosis, theranosis, and/or monitoring changes in a specific physiological state based on the comparison.

12. An in vitro process according to claim 11, wherein said analysis is of:

fluctuations in the sample target nucleic acid within the cell-free DNA to monitor response and/or resistance to medical treatment, or fluctuations in the sample target nucleic acid within the cell-free DNA to decide whether to conduct a subsequent analysis of genomic abnormalities, or changes in the concentration of mutated DNA in the sample target nucleic acid within the cell-free DNA interest.

13. A process according to claim 11, wherein said co-amplifying and/or quantifying steps comprise digital PCR, qPCR, and/or Next Generation Sequencing (NGS).

* * * * *